United States Patent [19]

Schenck

[11] Patent Number: 5,753,106
[45] Date of Patent: May 19, 1998

[54] METHOD OF, AND APPARATUS FOR, AND IRRADIATION UNIT FOR OXIDATIVE PHOTOPURIFICATION

[76] Inventor: Guenther Otto Schenck, Bismarckstrasse 31, 45470 Mülheim, Germany

[21] Appl. No.: 510,785

[22] Filed: Aug. 3, 1995

[51] Int. Cl.$^6$ .................................................. C02F 1/32
[52] U.S. Cl. .................. 210/96.1; 210/185; 210/199; 210/205; 210/192; 210/252; 210/748; 210/760; 422/24; 422/186.3; 250/432 R; 250/436
[58] Field of Search .................. 210/748, 760, 210/192, 85, 96.1, 185, 198.1, 199, 205, 252; 422/24, 186.3; 250/432 R, 436

[56] References Cited

U.S. PATENT DOCUMENTS

| | | | |
|---|---|---|---|
| 4,012,321 | 3/1977 | Koubek . | |
| 4,255,383 | 3/1981 | Schenck | 422/24 |
| 4,296,066 | 10/1981 | Schenck | 422/24 |
| 4,317,041 | 2/1982 | Schenck | 250/435 |
| 4,857,204 | 8/1989 | Joklik | 210/748 |
| 4,968,437 | 11/1990 | Noll et al. | 210/748 |
| 5,266,215 | 11/1993 | Engelhard | 210/748 |
| 5,290,439 | 3/1994 | Buchwald | 210/748 |
| 5,352,359 | 10/1994 | Nagai et al. | 210/748 |
| 5,501,801 | 3/1996 | Zhang et al. | 210/748 |
| 5,547,590 | 8/1996 | Szabo | 210/748 |

FOREIGN PATENT DOCUMENTS

| | | |
|---|---|---|
| 0179376 | 10/1985 | European Pat. Off. . |
| 2618338 | 11/1976 | Germany . |
| 4138421 | 12/1993 | Germany . |

OTHER PUBLICATIONS

"Die Beseitigung organischer Substanzen aus dem Wasser durch UV-Behandlung und Wasserstoffperoxid" (Removal of Organic Compounds from Water by UV-treatment and Hydrogen Peroxide) published in the Conference vol. entitled Oxidationsverfahren in der Trinkwasseraufbereitung (Oxidation Methods in Potable Water Processing) 1978, pp. 541–577 by L. Berglind, et al.

"UV radiation sources for oxidation of pollutants in liquids and gases" Schultz, Jens Peter, Dr., 1993 pp. 1–14.

"Chemical principles behind the use of UV-radiation and/or oxidants (ozone and hydrogen peroxide) in water pollution control", Sonntag, Clemens von, et al Jun. 1993, Introductory.

*Primary Examiner*—Neil McCarthy
*Attorney, Agent, or Firm*—Mallinckrodt & Mallinckrodt

[57] ABSTRACT

An annular throughflow photoreactor for oxidative photopurification includes an elongate radiation source surrounded by a transparent wall in the form of a spacer tube at a radial spacing of more than 3 cm, preferably in the range of more than 3 cm to 13 cm. The irradiance, i.e. the radiant flux per irradiated area is thereby reduced in comparison to a classic annular photoreactor. At unchanged irradiation power, this results in considerably increased quantum yields or extent of photoconversion in cases in which such conversion is dependent upon the square root of the irradiance, and thus enables enormous savings in radiation energy. Under such conditions, the photoconversion may be additionally increased by using low absorber concentrations and infeeding further absorber on the inside of the outer wall of the photoreactor as well as by working in the presence of gaseous oxygen at an oxygen pressure up to 3 bar and, preferentially, at pH 3. The throughflow photoreactor may comprise an annular single chamber or dual chamber photoreactor or a tank reactor having an annular array of irradiation units including the spacer tubes. A plural number of such photoreactors may be series connected.

40 Claims, 6 Drawing Sheets

METHOD OF, AND APPARATUS FOR, AND IRRADIATION UNIT FOR OXIDATIVE PHOTOPURIFICATION

BACKGROUND OF THE INVENTION

The invention relates to a method of oxidative purification of a medium which is transparent to optical radiation and which contains contaminants in the form of at least one oxidizable carbon compound. For oxidative purification, a radical forming "absorber" is added to the medium. Such "absorber", when exposed to the optical radiation, forms free radicals which initiate sequences of oxidizing radical reactions resulting in oxidation of the contaminants. The medium containing such radical forming absorber, is infed into a reaction chamber, which surrounds an elongate radiation source, and is exposed therein to the optical radiation emitted by the elongate radiation source.

The invention further relates to an apparatus for oxidative purification of a medium which is transparent to optical radiation and which contains contaminants in the form of at least one oxidizable carbon compound. The medium further contains an absorber which, when exposed to optical radiation, forms free radicals which initiate sequences of oxidizing radical reactions resulting in oxidation of the contaminants. The apparatus comprises an elongate radiation source which produces the optical radiation, and a reaction chamber surrounding the elongate radiation source and receiving the medium to be irradiated.

Also, the invention relates to an irradiation unit for use in conjunction with a reaction chamber for oxidative photopurification of a medium contaminated by at least one oxidizable carbon compound. The irradiation unit comprises an elongate radiation source which may be closely and coaxially surrounded by an envelope tube.

According to a method such as known, for example, from U.S. Pat. No. 4,012,321, granted Mar. 15, 1977, acetic acid and its salts, also trichloro acetates, can be oxidized to carbon dioxide and water when present in aqueous solution, by adding hydrogen peroxide and passing this solution through a throughflow reactor. Therein, the solution is exposed to UV radiation having a wavelength smaller than or equal to 260 nm.

From a publication by L. Berglind et al. entitled "Die Beseitigung organischer Substanzen aus dem Wasser durch UV-Behandlung und Wasserstoffperoxid" (Removal of Organic Compounds from Water by UV-treatment and Hydrogen Peroxide), published in the Conference Vol. entitled "Oxidationsverfahren in der Trinkwasseraufbereitung" (Oxidation Methods in Potable Water Processing), Editors W. Kuehn and B. Sontheimer, Karlsruhe 1978, pp. 541–577, it is known to add hydrogen peroxide to water which is contaminated by organic compounds including halogenated compounds, and circulating the thus pretreated water through a throughflow photoreactor. Considerable portions, sometimes the entirety, of the contaminants are degraded thereby.

A method of degrading noxious compounds like formaldehyde or its mixtures with methanol, formic acid and calcium formate in water, such as known, for example, from German Published Patent Application No. 4,138,421, published May 27, 1993, relies upon adding hydrogen peroxide to the noxious compound solution and exposing the same to UV radiation in a throughflow photoreactor. The employed throughflow photoreactors have diameters up to 100 cm and comprise up to 5 high pressure mercury lamps each having a power input of 1 or 2 kW. Also, a number of throughflow photoreactors may be connected in series. The reaction conditions are selected such that incident radiation of a wavelength of 265 nm is absorbed already in less than half the reactor volume so that more than half the reactor volume remains unirradiated. Under these conditions up to 81% of the formaldehyde present could be decomposed.

In a method of, and apparatus for, oxidative photopurification such as described, for example, in German Published Patent Application No. 2,618,338, published Nov. 11, 1976, there are provided a plural number of essentially identically constructed contact zones which are series-connected in the throughflow direction of the water to be purified. Ozone containing gas is passed through the contact zones in countercurrent fashion. Each one of the contact zones is provided with a UV radiation source emitting, for example, at a wavelength of 254 nm. The combined effect of UV radiation and ozone are used for oxidizing to carbon dioxide and water any refractory organic compounds like acetic acid which are present in the treated water in concentrations up to 0.1 per mil.

Many organic compounds represent environmentally harmful compounds which are toxic and must be present in potable water only in comparatively very low amounts but which are presently contained in groundwater in quantities which exceed the acceptable extent. Examples thereof are organic chlorinated compounds, particularly chlorinated hydrocarbons containing 1 and 2 carbon atoms, which are desired as solvents but which can be toxic, carcinogenic and mutageneous. According to EC regulations, such compounds must not be present in potable water in amounts above 1 μg per liter. Due to their particular properties, these compounds represent indispensable technological auxiliaries while they are dreaded in view of their harmful environmental effects.

The purification of saturated aqueous solutions particularly of the various chlorinated hydrocarbons and fluorochlorinated hydrocarbons which solutions summarily may contain in the range of 0.6 to 1.5 g/l of chlorinated organic compounds, is fraught with problems because the hitherto employed methods (biodegradation; combustion) have turned out to be either insufficient or problematic. Presently used photochemical methods and apparatuses employ radiation sources which are surrounded by an envelope tube having the smallest possible diameter, and a cooling jacket having a thickness of only a few millimeters. The reason therefore is to provide the smallest possible cooling chamber and to keep the costs of the water-cooled irradiation unit at a minimum. However, it has now been found that such units are less suitable from the point of energy consumption, for effecting photomineralization of contaminants which are present in water only at low concentrations, or photochemical purification of water in the presence of radical forming absorbers.

To begin with, the invention is based on the recognition that, when carrying out the presently considered reactions, peroxi compounds are photochemically dissociated into highly reactive oxidizing radicals. Such oxidizing radicals react with the contaminants which are intended to be degraded or mineralized, in radical chain reactions or oxidation sequences which are known as such. In the following diagrammatic representation which is restricted to some essential steps of such radical chain reactions, exemplary individual reactions are shown which participate in the radical chain oxidation.

TABLE I

Important Reaction Steps in Oxidative Photopurification

I. Initiation: Radical Formation

| | | | |
|---|---|---|---|
| $H_2O_2 + h\nu$ | $= 2\ HO^\bullet$ | | Unsensitized $H_2O_2$ Photolysis |
| $TiO_2 + H_2O_2 + h\nu$ | $= TiO_2^+ + HO^- + HO^\bullet$ | | Sensitized $H_2O_2$ Photolysis |
| $S_2O_8^{2-} + h\nu$ | $= 2\ {}^\bullet OSO_3^-$ | | Persulphate Photolysis |

II. Propagation: a) abstractive and
b) additive propagation reactions

| | | | |
|---|---|---|---|
| a) R—H | + ${}^\bullet OH$ | = HOH + R${}^\bullet$ | |
| R${}^\bullet$ | + $O_2$ | = R—O—O${}^\bullet$ | Peroxi Radical (in the Presence of $O_2$) |
| R—O—O${}^\bullet$ | + H—R | = R—O—O—H | R-Hydroperoxide + R${}^\bullet$ |
| b) C=C | + ${}^\bullet OH$ | = ${}^\bullet$C—C—OH | |
| $O_2$ | + ${}^\bullet$C—C—OH | = ${}^\bullet$O—O—C—C—OH | Peroxiradical |
| C=C | + ${}^\bullet$O—O—C—C—H | = ${}^\bullet$C—C—O—O—C—C—OH | Copolymerization with $O_2$ | c) Interfering Scavenging Reactions

| | | |
|---|---|---|
| ${}^\bullet OH + H_2O_2$ | $= H_2O + HO_2^\bullet$ | $H_2O_2$ as Scavenger for ${}^\bullet OH$ |
| ${}^\bullet OH + HCO_3^-$ | $= H_2O + CO_3^{\bullet -}$ | Low Oxidation Pot., ready Self-Termination at higher Conc. |
| ${}^\bullet OH + CO_3^{2-}$ | $= H_2O + CO_3^{\bullet -}$ | |

III. Termination

| | | |
|---|---|---|
| $2\ HO^\bullet$ | $= H_2O_2$ | (Re) Combination |
| $2\ HO_2^\bullet$ | $= H_2O_2 + O_2$ | Disproportionation |
| $2\ R^\bullet$ | $= R—R$ | Combination |
| $2\ {}^\bullet$O—O—C—C—H | $= H—C—C—O—O—C—C—H + O_2$ | Disproportionation |

According to the foregoing reaction scheme, the radicals which are formed as a result of photolysis of the peroxi compounds, constitute the effective agent attacking the contaminants which are only schematically indicated by RH and C=C. The intermediates formed thereby are, in turn, very reactive radicals entering into subsequent reactions which are not specifically indicated but which are also known as such. These subsequent reactions result in the desired degradation or mineralization, particularly in the presence of oxygen which is formed from the hydrogen peroxide or which may be separately introduced as such into the medium prior to or during irradiation.

The invention further starts from the recognition that the oxidative photopurification as illustrated in the foregoing reaction scheme, can be carried out at increased efficiency when the competition of the terminating and scavenging reactions with the radical propagation reactions is reduced. The rate of the radical propagation reactions is proportional to the stationary concentration of the radicals which are photolytically formed from the absorber and initiate the radical chain oxidation. During photolysis of hydrogen peroxide, the hydroxyl radical is formed at a formation rate defined by $$+V_{OH} = I \cdot k_1 \cdot [H_2O_2];$$

therein, I is the irradiation intensity and $k_1$ is the quantum yield of photolysis which is assumed to be equal to 1 in the present instance.

The thus obtained hydroxyl radicals disappear in a termination reaction which is essentially determined by the (re)combination which occurs at the rate of $$-V_{OH} = k_2 \cdot [OH]^{1/2}.$$

Then, the stationary concentration of the intermediate hydroxyl radicals is determined by equality of the rates of formation and disappearance, viz.

$$+V_{OH} = -V_{OH}.$$

It will follow therefrom that the stationary concentration of hydroxyl radicals, i.e. the radicals which effect the propagation reactions resulting in the desired degradation and mineralization, is given by the following relationship $$[OH]_{sta} = \sqrt{\frac{k_1}{k_2} \cdot I \cdot [H_2O_2]}$$

It will be seen from the foregoing reaction scheme that not only the recombination of the hydroxyl radicals but also their reaction with hydrogen peroxide will compete with the desired propagation reaction when hydrogen peroxide is added in excessive concentration. On the other hand, however, the absorption of the incident radiation by hydrogen peroxide is comparatively low in the generally accessible wavelength range: thus, the value of the decadic molar absorption coefficient of hydrogen peroxide is only 19 lmol$^{-1}$ cm$^{-1}$ at the wavelength of 254 nm. Therefrom, the desire results for high concentrations in order to achieve high absorption of the effective radiation but such desire is counterproductive regarding the desired propagation because, under such conditions, the scavenging reaction according to reaction IIc. and the bimolecular termination reaction according to section III. in the foregoing reaction scheme become favored.

The invention, furthermore, is based on the recognition that the square root dependency of the photostationary hydroxyl radical concentration on the irradiation intensity as well as the hydrogen peroxide concentration basically distinguishes the conditions of oxidative photopurification from those prevailing in the case of photodisinfection, see, for example, U.S. Pat. No. 4,255,383, granted Mar. 10, 1981. According to the Grotthus-Draper Law only photons which are absorbed essentially by the DNA within the microorganisms, will cause photodisinfection. These photons act in accordance with the Bunsen-Roscoe Law according to which the effect of UV-inactivation is proportional to the radiation intensity and the irradiation duration, i.e. the UV dose. As seen from this relationship, the effect is independent of the irradiance, i.e. the radiant flux per irradiated area.

In the present instance, as already explained hereinbefore, the rate of oxidative photopurification is dependent on the square root of the radiation intensity and thus also on the square root of the irradiance. As shown in the following Table II, the square root of the irradiance (as well as the square root of the initial radical concentration) decreases less than the irradiance with increasing radial distance from the elongate radiation source. As a consequence, the reaction rate of oxidative photopurification increases with increasing radial distance from the radiation source by a gain factor GF which is defined as follows $$GF = \sqrt{\frac{\text{Irradiance, 3 cm}}{\text{Irradiance, } x \text{ cm}}} = \sqrt{\frac{\text{Radial Distance, } x \text{ cm}}{\text{Radial Distance, 3 cm}}}$$

and which is shown in the right-hand column of Table II.

Thus it is shown that the simple geometric measure of increasing the radial distance of the reaction chamber from the elongate radiation source results in an increase in the rate of oxidative photopurification. According to Table II, the rate of oxidative photopurification will increase by a factor in the range of 1.155 to 4.082 when the radial distance of the reaction chamber from the elongate radiation source is increased from 3 cm to the range of 4 cm to 50 cm.

TABLE II

Irradiance and Gain Factor GF as a Function of Radial Distance in an Annular Photoreactor
(Radiation Source: Arc Length 100 cm; Emission 15 W/cm)

| Radial Distance cm | Irradiated Surface Area cm$^2$ | Irradiance W/cm$^2$ | $\sqrt{\text{Irradiance}}$ W/cm$^2$ | Gain Factor GF |
|---|---|---|---|---|
| 3 | 1,884 | 0.7962 | 0.8923 | |
| 4 | 2,512 | 0.5971 | 0.7727 | 1.155 |
| 5 | 3,140 | 0.4777 | 0.6912 | 1.291 |
| 6 | 3,768 | 0.3981 | 0.6310 | 1.414 |
| 7 | 4,396 | 0.3412 | 0.5841 | 1.527 |
| 8 | 5,024 | 0.2986 | 0.5464 | 1.633 |
| 9 | 5,652 | 0.2654 | 0.5152 | 1.732 |
| 10 | 6,280 | 0.2389 | 0.4888 | 1.852 |
| 15 | 9,420 | 0.1592 | 0.3990 | 2.236 |
| 20 | 12,560 | 0.1194 | 0.3455 | 2.582 |
| 50 | 31,400 | 0.0477 | 0.2186 | 4.082 |

As a consequence, photoreactors for oxidative photopurification will have to be constructed and operated differently from the known photoreactors used for photodisinfection. In the latter, according to U.S. Pat. No. 4,296,066, granted Oct. 20, 1981, the penetration depth or thickness is selected such that 56.3% of the incident radiation are absorbed in order to ensure optimum results. Contrary thereto, in order to achieve optimum results in oxidative photopurification, it should be endeavoured that the highest possible amount of radiation is absorbed at the lowest possible absorbance.

Hitherto the square root dependency of the oxidative photopurification on the irradiance intensity and the concentration of the radical forming absorber has not been taken into account in the construction and operation of technical throughflow photoreactors, see, for example, the publication by J. P. Schulz entitled "UV-Strahlungsquellen zur Oxidation von Schadstoffen in Flüssigkeiten und Gasen" (UV Radiation Sources for Oxidation of Harmful Compounds in Liquids and Gases), published in the CUTEC Publication Series, entitled "Naβoxidative Abwasserbehandlung, Forschung-Entwicklung-Stand der Technik" (Wet Oxidative Waste Water Treatment, Research-Development-State of the Art) by Clausthaler Umweltakademie, Editor A. Vogelpohl, 1993, pp. 1 to 14. Therein, conventional photoreactors are used which have a thickness in the range of 4 cm to 5 cm and which immediately adjoin the envelope tube of the radiation source, and relatively high concentrations of hydrogen peroxide are employed. Also, the introductory paper by Cl. V. Sonntag therein which is entitled "Chemical Principles Behind the Use of UV-Radiation and/or Oxidants (Ozone and Hydrogen Peroxide) in Water Pollution Control", did not include any indication regarding the possibilities offered by the aforementioned square root dependency as a technical key function.

SUMMARY OF THE INVENTION

Therefore, with the foregoing in mind, it is a primary object of the present invention to provide a new and improved method of, and an apparatus for, oxidative photopurification and which method and apparatus are not afflicted with the drawbacks and limitations of the prior art heretofore discussed.

Another and more specific object of the invention is directed to the provision of a new and improved method and apparatus which permit optimum utilization of the radiation emitted by the radiation source for the process of oxidative photopurification.

It is an important object of the invention to provide a new and improved method and apparatus which ensure optimum utilization of the radical forming absorber in the process of oxidative photopurification for the degradation of oxidizable carbon compounds which are present in the irradiated medium.

A further, highly significant of object of the invention is directed to providing a new and improved method and apparatus for oxidative photopurification readily permitting the concentration of harmful substances like chlorinated organic compounds in the irradiated medium to be reduced at least to the accepted limits.

It is still an important object of the invention to provide a new and improved method and apparatus for carrying out the oxidative photopurification at high irradiation power and throughflow rates in order to achieve high degradation rates of contaminants in more highly contaminated aqueous media.

Now, in order to implement these and still further objects of the invention, which will become more readily apparent as the description proceeds, the method of, and apparatus for, oxidative photopurification according to the present deveolopment are manifested by the feature that, among other things, a transparent wall which is transparent for the effective optical radiation, is arranged at a radial spacing of more than 3 cm from the lengthwise axis of the elongate radiation source. This spacing advantageously is in the range of more than 3 cm to 13 cm, preferably 4 to 9 cm. The optical radiation is passed through the transparent wall into a reaction chamber containing the medium to be irradiated, i.e. the medium which as such is transparent to the optical radiation, which is contaminated by at least one oxidizable carbon compound, and which contains the absorber forming free radicals and initiating sequences of oxidizing radical reactions upon exposure to the optical radiation emitted by the elongate radiation source.

A preferred throughflow photoreactor for reducing the COD of more highly contaminated media by oxidative photopurification, constitutes a substantially vertically disposed, substantially cylindrical tank reactor having an inlet and an outlet. Therein, the elongate radiation source comprises an annular array of irradiation units which array extends at a predetermined radial spacing from and substantially parallel to the central longitudinal axis of the tank reactor. Each one of the irradiation units includes an elongate radiation source which is surrounded by a transparent wall in the form of a spacer tube at a radial spacing of more than 3 cm, preferably in the range of more than 3 cm to 13 cm, and most preferred in the range of 4 cm to 9 cm from the lengthwise axis of the elongate radiation source.

As alluded to above, the present invention is not only concerned with the new and improved method of, and apparatus for, oxidative photopurification but also an irradiation unit for use in conjunction with such method and apparatus. The irradiation unit comprises an elongate radiation source which may be housed in an envelope tube closely and coaxially surrounding the same. In order to achieve the aforementioned objects, the elongate radiation source is coaxially surrounded by a transparent wall in the form of a spacer tube at a radial spacing of more than 3 cm, preferably in the range of more than 3 cm to 13 cm, and most preferred in the range of 4 cm to 9 cm from the lengthwise axis of the elongate radiation source.

In accordance with the inventive method and apparatus practically the entire radiation emitted by the radiation source, will enter the reaction chamber at a comparatively reduced irradiance whereby the aforementioned propagation reactions are favored relative to the termination and scavenging reactions so that the efficiency and quantum yields of the overall process are increased.

The reaction chamber may constitute a throughflow reactor, particularly an annular single chamber or dual chamber throughflow photoreactor wherein the transparent wall is incorporated in the side facing the elongate radiation source. The favorable effect of the lower irradiance can be utilized, for example, for the oxidative photopurification of ground water from chlorinated hydrocarbons and for the attainment of high purity degrees. Consequently, the active species will be more uniformly distributed throughout the medium under irradiation due to the square root dependency on the irradiance. The total process efficieny is significantly increased thereby. This has the important result that the contaminants can be degraded to an extent which covers many powers of ten; for example, in the case of chlorinated hydrocarbons in ground water, the irradiation product can be produced in a purity satisfying EC standards of <1 µg/l AOX (Adsorbable Organic Halogenated Compounds).

Frequently, it is not reasonable to irradiate the oxidizing radical forming absorber and the organic contaminants from the beginning either in the required stoichiometric ratio or at a stoichiometric excess of such absorber. For example, in the case of leakage water leaking from waste dumps and depending on the respective COD values, relatively high absorber concentrations may be required if stoichiometric absorber proportions are desired. In such cases most of the incident radiation would become absorbed within the first few millimeters of the layer of the irradiated medium which can be disadvantageous with respect to the exchange of matter and heat. Additionally, the quantum yield, as pointed out hereinbefore, is dependent upon the absorber concentration according to a square root function. For the reasons discussed hereinabove it will be preferable to adjust the absorber concentration in the medium to lower values and continuously resupply the consumed absorber during irradiation. Instead, the oxidative purification may be carried out in a plural number of series-connected throughflow photoreactors.

BRIEF DESCRIPTION OF THE DRAWINGS

The invention will be better understood and objects other than those set forth above, will become apparent when consideration is given to the following detailed description thereof. Such description makes reference to the annexed drawings wherein the same or analogous components are designated by the same reference numerals and wherein.

DETAILED DESCRIPTION OF THE PREFERRED EMBODIMENTS

Describing now the drawings, it will be understood that only enough of the construction of throughflow photoreactors has been shown as needed for those skilled in the art to readily understand the underlying principles and concepts of the present development, while simplifying the showing of the drawings. While the illustrated throughflow photoreactors are described herein in conjunction with certain absorbers and the oxidative photopurification of water from specific contaminants, it should be noted that these are described herein merely as a matter of example in order to fully explain the favorable effects which can be achieved when utilizing the invention. It will be appreciated that the invention is not limited to the absorbers and contaminants which are particularly mentioned in connection with the following examples.

Figure 1:
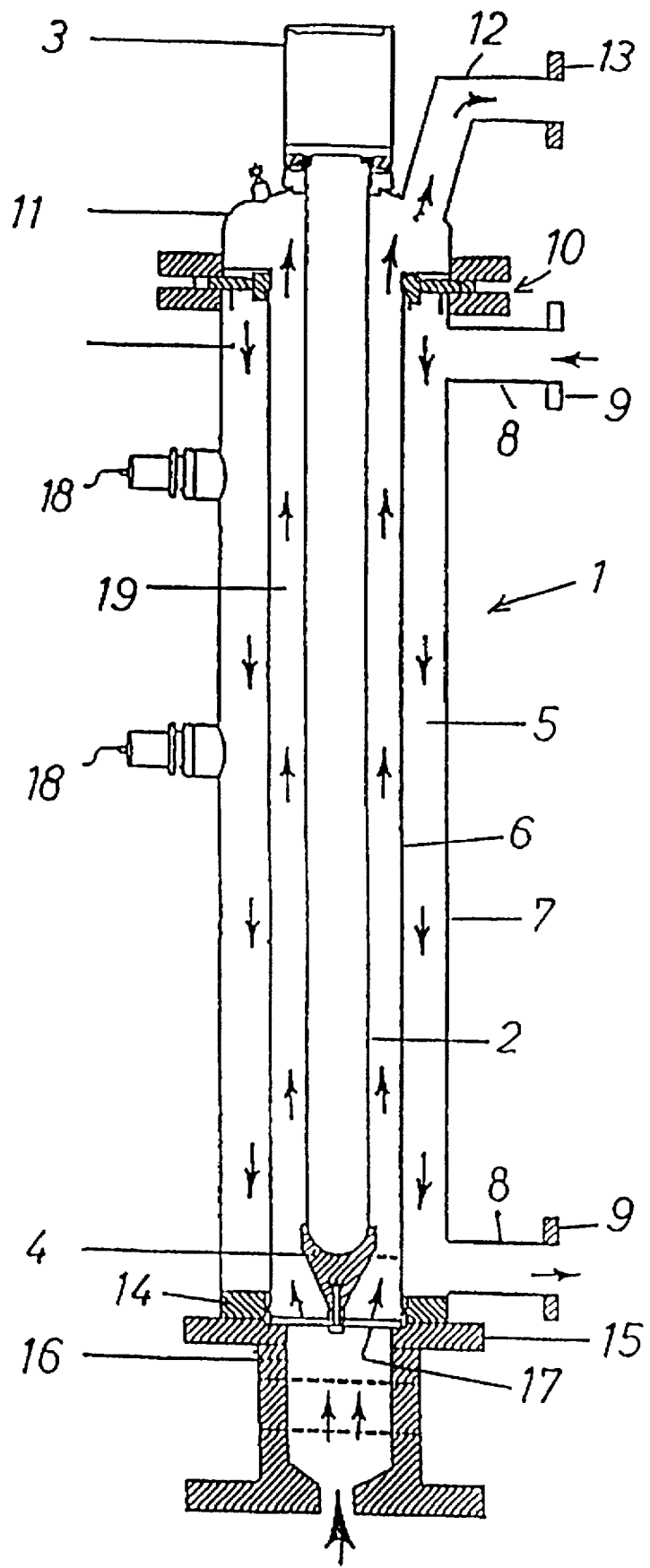
FIG. 1 is a schematic longitudinal section through a first exemplary embodiment of the invention in the form of an annular single chamber throughflow photoreactor which can be employed for carrying out the inventive method.

With reference to FIG. 1, there is schematically shown therein in longitudinal section a first exemplary embodiment of the inventive throughflow photoreactor. The throughflow photoreactor comprises an annular single chamber photoreactor 1 including a quartz envelope tube 2 intended for housing a conventional and, therefore, not illustrated elongate radiation source. Such radiation source may include, for example, one or more medium pressure mercury lamps having a power input of 10 to 250 W per cm of the arc length. Instead, there may also be used, for instance, low pressure mercury lamps, high pressure mercury lamps, doped mercury lamps, doped high pressure xenon lamps etc.

At its open top end, the envelope tube 2 is provided with means 3 for retaining and connecting the elongate radiation source. The bottom end of the envelope tube 2 is closed and rests at a support 4. The actual irradiation chamber 5 of the annular single chamber photoreactor 1 is formed by means of a quartz tube 6 and a stainless steel tube 7. The quartz tube 6 constitutes a transparent wall or spacer tube which distances the irradiation chamber 5 from the envelope tube 2 housing the elongate radiation source. The outer stainless steel tube 7 carries connectors 8 at its opposite ends and these connectors 8 are provided with connection flanges 9 for connection to infeed and outfeed conduits or lines for the medium to be irradiated. At their top ends, the quartz tube or spacer tube 6 and the stainless steel tube 7 are sealingly connected to the top end of the envelope tube 2 and a closure member 11 by means of a conventional flange connection 10. The envelope tube 2 extends through the closure member 11 which is provided with a connector 12 and a connecting flange 13 for the throughpassage of a protective gas. The lower ends of the quartz tube or spacer tube 6 and the stainless steel tube 7 are sealingly connected in the usual manner through a sealing body 14 to a connecting flange 15 of a connector 16 serving for the throughpassage of protective gas. Preferably, the medium to be irradiated and the protective gas are passed through the single chamber photoreactor 1 in countercurrent fashion.

The connecting flange 15 accommodates an apertured plate 17 at which the support 4 for supporting the lower end of the envelope tube 2 is supported. One radiation sensor or as illustrated in the example, two radiation sensors 18 are laterally attached to the outer stainless steel tube 7 and serve for measuring the transmission of the irradiated medium. This measurement permits monitoring, on the one hand, the operation of the radiation source and, on the other hand, controlling the throughflow of the medium to be irradiated as will be further explained hereinbelow.

EXAMPLE 1

In one embodiment of the annular single chamber throughflow photoreactor 1 as shown in FIG. 1, the envelope tube 2 has an outer radius of 3 cm or an outer diameter of 6 cm; the transparent or spacer tube 6, which is made of quartz glass, has an inner radius of 6.68 cm or outer diameter of 14 cm and a wall thickness of 0.32 cm; and the stainless steel tube 7 has an inner radius of 12 cm or an outer diameter of 24 cm. There is thus formed an annular single chamber throughflow photoreactor 1 in which the transparent wall or spacer tube 6 defines a distance chamber 19 having a thickness of 3.68 cm between the envelope tube 2 and the reaction or irradiation chamber 5 which is formed by the transparent wall or spacer tube 6 and the stainless steel tube 7. The thickness of the irradiation chamber 5, then, is 5 cm. At a total length of 100 cm the irradiation chamber 5 has a volume of 29.8 liter. On the basis of these data and a linear throughflow rate of 1 meter per second, a throughflow of 107.4 m³ per hour is computed. A 5.8 kW medium pressure mercury lamp having an arc length of 60 cm is placed in the envelope tube 2.

A saturated aqueous solution containing 140 mg/l corresponding to 1.05 mmol/l of 1,1,1-trichloroethane is investigated. The concentration of trichloroethane is determined by gas chromatography prior to and after irradiation. A 50% aqueous solution of hydrogen peroxide was added to the aqueous trichloroethane solution in an amount resulting in a concentration of 0.1 g/l which corresponds to 2.95 mmol/l. Hydrogen peroxide and trichloroethane react in the overall reaction

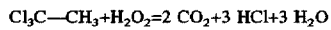

The composition of the aforementioned solution very closely approximates the requirements of the equation for this reaction.

The distance chamber 19 is throughpassed by a slow flow (3 to 10 l/h) of high purity nitrogen in order to prevent any harmful effects of oxygen. After run-in of the elongate radiation source, the aforementioned aqueous solution is passed through the annular single chamber throughflow photoreactor 1 at a flow rate of 180 l/h. Under these conditions, the efflux contained 25 µg/l of 1,1,1-trichloroethane so that the concentration thereof has been reduced by a factor of $1.786 \cdot 10^{-4}$; the electric current consumption amounted to 32.2 kWh/m³.

EXAMPLE 2

In a comparative experiment, the same aqueous solution was flown through a conventional single chamber photoreactor devoid of the distance chamber so that the irradiation chamber immediately adjoined the envelope tube in the general direction of irradiation. The envelope tube had an outer radius of 3 cm or an outer diameter of 6 cm; the irradiation chamber was defined by the envelope tube and an outer tube having an inner radius of 8 cm or an outer diameter of 16 cm. Therefore, the irradiation chamber likewise had a thickness of 5 cm and, at a length of 100 cm, a volume of 17.27 liter. At the linear flow rate of 1 m/sec the throughflow amounts to 62.2 m³/h. The same radiation source and the same solution were used in the experiment.

At a throughflow of 130 l/h and an electric current consumption of 45 kWh/m³ the concentration of 1,1,1-trichloroethane was reduced by a factor of $1.876 \cdot 10^{-4}$ to 25 µg/l corresponding to 0.187 µmol/l.

A comparison of the results obtained in Examples 1 and 2 teaches the following: In both Examples the thickness of the irradiation chamber amounted to 5 cm. The radiation is absorbed by 1,1,1-trichloroethane in the effective wavelength range of the Examples only in an amount which is negligible in comparison to the absorption by the hydrogen peroxide. The decadic logarithmic absorption coefficient of hydrogen peroxide at 254 nm is 19 lmol⁻¹ cm⁻¹ and the concentration used in the Examples is 2.94 mmol/l so that, at the thickness of 5 cm, the initial absorbance amounts to 0.2793. Accordingly, at the wavelength of 254 nm, 52.6% of the incident radiation are transmitted and 47.4% of the incident radiation are absorbed by the solution at the start of the experiments. In comparison to Example 2, the irradiance is reduced in Example 1 due to the presence of the transparent wall or spacer tube 6 or the distance chamber 19 and the increase in the irradiated surface area caused thereby. Nevertheless a considerably improved result is achieved in Example 1 in the presence of the transparent wall 6 or the distance chamber 19: regarding the throughflow or the electric current consumption, the result is improved by a factor of 1.39. This surprising result has been obtained although the same amount of radiative energy has been absored in both of the Examples.

Quite similar results are obtained when tetrachloroethene is used instead of 1,1,1-trichloroethane. The aqueous solution contained 90 µg/l corresponding to 0.542 mmol/l of tetrachloroethene and 0.1 g/l corresponding to 2.94 mmol/l of hydrogen peroxide. The overall reaction is

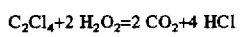

Using the classic single chamber photoreactor as in Example 2 and a 7.5 kW medium pressure mercury lamp, tetrachloroethene was degraded to a residual concentration of 1.25 µg/l at a throughflow of 130 l/h and an electric current consumption of 57.7 kWh/m³. In the annular single chamber throughflow photoreactor 1 containing the transparent wall 6 or the distance chamber 19 as in Example 1, a degradation was achieved down to a residual concentration of 0.2 to 0.4 µg/l at the same throughflow of 130 l/h and the same electric current consumption of 57.7 kWh/m$^3$. The presence of the transparent wall 6 or the distance chamber 19 thus results in an improvement in the degradation effect by a factor of 3 to 6.

EXAMPLE 3

The input side of the classic single chamber photoreactor as in Example 2 was connected to a mixing chamber. Therein, a concentrated aqueous solution of sodium persulphate was metered to a saturated aqueous solution containing 350 mg/l corresponding to 2.68 mmol/l of trichloroethene to an extent such that the transmission, which was measured by an instrument placed at the output of the mixing chamber, amounted to 0.75 at 254 nm and a thickness of 1 cm. Under these conditions and considering the 5 cm thickness of the irradiation chamber, 88.1% of the incident radiation are absorbed. At a throughflow of 160 l/h and an electric current consumption of 36.25 kWh/m$^3$, the trichloroethene was degraded down to a residual concentration of 25 µg/l.

Figure 2:
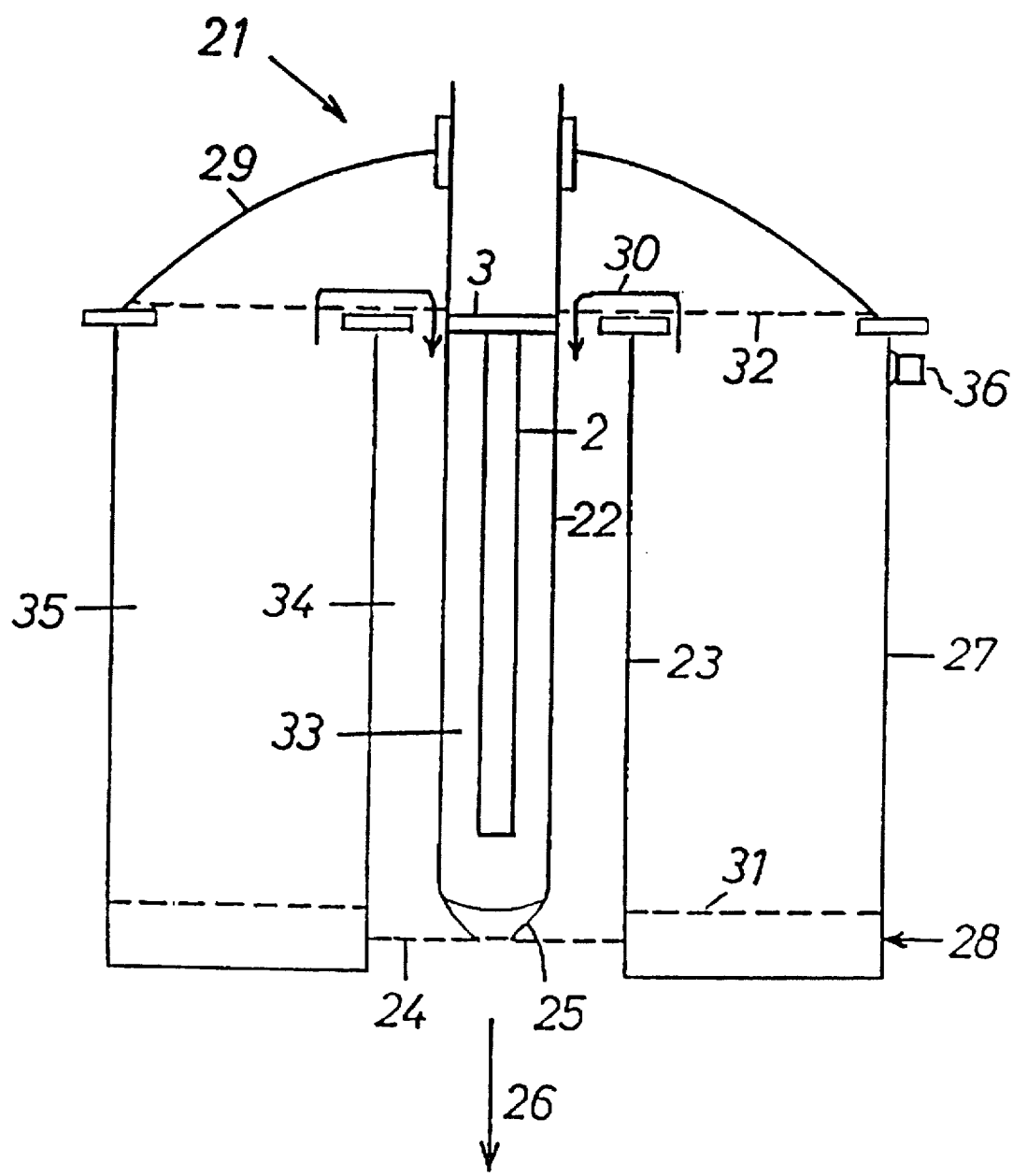
FIG. 2 is a schematic longitudinal section through a second exemplary embodiment of the invention in the form of an annular dual chamber throughflow photoreactor which can be employed for carrying out the inventive method.

FIG. 2 schematically shows a longitudinal section through a second exemplary embodiment of the inventive apparatus in the form of an annular dual chamber throughflow photoreactor 21. Various constructions of such dual chamber photoreactors are known as such from U.S. Pat. Nos. 4,255,383, granted Mar. 10, 1981; 4,296,066, granted Oct. 20, 1981; and 4,317,041, granted Feb. 23, 1982, to the inventor of the instant application and, therefore, will be subsequently described only with respect to the details which are important with respect to the subject of the present application.

The annular dual chamber throughflow photoreactor 21 as depicted in FIG. 2 includes the same type of elongate radiation source (not illustrated) and the same envelope tube 2 like the annular single chamber throughflow photoreactor 1 shown in FIG. 1. As described hereinbefore with respect to the single chamber photoreactor 1, the dual chamber photoreactor 21 has an envelope tube 2 which is provided with retaining and connecting means 3 for retaining and connecting the radiation source. The envelope tube 2 is coaxially surrounded by a transparent wall in the form of a spacer tube 22 which is made of quartz glass and closed at its bottom end. The top end of the spacer tube 22 is held by the retaining and connecting means 3 and provided with connectors (not shown) for throughpassing the aforementioned slow flow of highest purity nitrogen. The transparent wall or spacer tube 22, in turn, is coaxially surrounded by a separating tube 23 made of quartz. The bottom end of the separating tube 23 is closed by means of an apertured plate 24 to which a support 25 for the closed bottom end of the transparent wall or spacer tube 22 may be attached. The bottom end of the separating tube 23 leads to a discharge 26 for irradiated medium which discharge is of conventional construction and, therefore, only schematically indicated by an arrow. The separating tube 23 is coaxially surrounded by an outer tube 27 having a bottom end which is sealingly connected to the separating tube 23 and contains an inlet 28 for the medium to be irradiated. The inlet 28 is of conventional construction and, therefore, only schematically indicated by an arrow. The top end of the outer tube 27 protrudes beyond the top end of the separating tube 23 and is sealingly closed by means of a closure 29 which is only schematically illustrated because of its conventional construction. The closure 29 extends at a spacing from the top end of the separating tube 23 and is sealingly connected to the transparent wall or spacer tube 22. There is thus formed an overflow 30 as indicated by an arrow. In order to render a substantially uniform throughflow, apertured plates 31 and 32 are respectively retained above the inlet 28 and above the overflow 30 within the closure 29.

The annular dual chamber throughflow photoreactor 21 thus is seen to include a distance chamber 33 which is formed between the envelope tube 2 and the transparent wall or spacer tube 22, an inner irradiation chamber 34 with respect to the elongate radiation source, which inner irradiation chamber 34 is formed between the transparent wall or spacer tube 22 and the separating tube 23, and an outer irradiation chamber 35 with respect to the elongate radiation source, which outer irradiation chamber 35 is formed between the separating tube 23 and the outer tube 28.

EXAMPLE 4

In one constructional design of the annular dual chamber throughflow photoreactor 21 according to FIG. 2, the envelope tube 2 has an outer radius of 2.5 cm or an outer diameter of 5 cm; the transparent wall or spacer tube 22 has an outer radius of 4.17 cm or an outer diameter of 8.34 cm; the separating tube 23 has an inner radius of 6.5 cm and an outer radius of 6.82 cm or an outer diameter of 13.64 cm; and the outer tube 28 has an outer radius of 26.8 cm or an outer diameter of 53.6 cm. There thus result a thickness of 1.35 cm for the distance chamber 33, a thickness of 2.33 cm for the inner irradiation chamber 34, and a thickness of 20 cm for the outer irradiation chamber 35. At a total length of 100 cm, the inner irradiation chamber 34 has a volume of 7.8 liter and the outer irradiation chamber 35 has a volume of 211 liter.

A saturated aqueous solution containing 130 mg/l corresponding to 0.784 mmol/l of tetrachloroethene and 0.05 g/l corresponding to 1.47 mmol/l of hydrogen peroxide is consecutively passed through the irradiation chambers 35 and 34. Due to the hydrogen peroxide contained therein, this solution absorbs 75.5% of the incident radiation in the total thickness of 22 cm at the start of the irradiation. At a throughflow of 120 l/h and an electric current consumption of 48.3 kWh/m$^3$, the irradiated solution contains a residual concentration of 3.0 µg/l corresponding to 0.15 µmol/l of tetrachloroethene.

In a comparative experiment using a classic single chamber photoreactor according to Example 2, but at a thickness of 7.4 cm and a concentration of 0.1 g/l corresponding to 2.94 mmol/l of hydrogen peroxide at the start of the irradiation, the tetrachloroethene is degraded to a residual concentration of 25 µg/l at a throughflow of 65 l/h and an electric current consumption of 89.2 kWh/m$^3$.

In a further comparative experiment using a single chamber photoreactor containing a distance chamber as described hereinbefore with reference to Example 1, the distance chamber had a thickness of 4 cm, the irradiation chamber had a thickness of 7.4 cm, and hydrogen peroxide was present at a concentration of 0.1 g/l corresponding to 2.94 mmol/l at the start of the irradition. The same residual tetrachloroethene concentration of 25 µg/l was obtained at a throughflow of 95 l/h and an electric current consumption of 61 kWh/m$^3$. In comparison to the comparative experiment described just above, this corresponds to an improvement by a factor of 1.46 or by 46%.

In relation to the aforedescribed comparative experiments, there is thus achieved a significant improvement in the throughflow when the annular dual chamber throughflow photoreactor 21 is employed, namely by a factor of 1.86 or 86% over the classic single chamber photoreactor. Also in relation to the annular single chamber throughflow photoreactor 1 which includes a distance chamber, there is still achieved an improvement factor of 1.26 or 26% in respect of the throughflow. In this connection it must be noted that the concentration of hydrogen peroxide in the case of the annular dual chamber throughflow photoreactor 21 is only one half at the start of the irradiation whereas the residual concentration of tetrachloroethene is further reduced, namely by a factor of 8, as compared to the classic single chamber photoreactor.

EXAMPLE 5

The inlet 28 of the annular dual chamber throughflow photoreactor 21 as shown in FIG. 2 is connected to a mixing chamber. Therein, a concentrated aqueous solution of sodium persulphate was metered to a saturated aqueous solution containing 350 mg/l corresponding to 2.68 mmol/l of trichloroethene to an extent such that the transmission, which was measured by an instrument placed at the output of the mixing chamber, amounted to 0.91 at 254 nm and a thickness of 1 cm. 89% of the incident radiation is absorbed by the solution at the total thickness of 22 cm. At a throughflow of 380 l/h and an electric current consumption of 15.3 kWh/m$^3$, the concentration of trichloroethene was reduced to 25 µg/l in correspondence with a reduction factor of $7.14 \cdot 10^{-5}$. At a lesser throughflow of 250 l/h and a higher electric current consumption of 23.2 kWh/m$^3$, the residual trichloroethene concentration amounted to only 0.9 µg/l which corresponds to a reduction factor of $2.57 \cdot 10^{-6}$ or a reduction in the concentration by nearly 6 powers of ten.

In comparison to Example 3 in which a single chamber photoreactor without distance chamber was used, the employment of the annular dual chamber throughflow photoreactor 21 thus achieves an improvement by a factor of 2.375 or by 137.5% although the sodium persulphate was present at lower concentration and less radiation was absorbed.

The annular single and dual chamber throughflow photoreactors of the aforedescribed embodiments are preferably arranged in vertical disposition. Such reactors may be provided with a distance chamber 19 or 33 which is defined by the transparent wall or spacer tube 6 or 22, respectively, and the envelope tube 2 which has a thickness in the range of 0.5 cm and 10 cm, preferably between 0.5 cm and 6 cm. In a not particularly illustrated modification, the envelope tube 2 is dispensed with and the elongate radiation source is arranged coaxially within the transparent wall or spacer tube 6 of the annular single chamber throughflow photoreactor 1 or the transparent wall or spacer tube 22 of the annular dual chamber throughflow photoreactor 21. The thereby formed spacing defines a radial distance between the lengthwise axis of the elongate radiation source and the spacer tube 6 or 22, as the case may be, in the range of more than 3 cm to 13 cm, preferably between 4 cm and 9 cm. In this manner the envelope tube 2 may be omitted without the risk of overheating of the elongate radiation source. This is due to the fact that the space between the elongate radiation source and the increased irradiated surface area is larger, which irradiated surface area is cooled by the throughflowing medium during irradiation while the throughflowing medium also is not subject to excessive local heating. In order to achieve protection from harmful effects of oxygen, the aforementioned slow flow of highest purity nitrogen is passed through the spacing also in these constructions.

Preferably, the annular dual chamber throughflow photoreactor 21 is constructed such that the thickness ratio of the outer irradiation chamber 34 to the inner irradiation chamber 35 is in the range of 3:1 to 40:1. The throughflow therein is effected in countercurrent fashion whereby the medium to be irradiated enters the outer irradiation chamber 35.

The throughflow operation in the aforedescribed annular single chamber or dual chamber throughflow photoreactors may be controlled by means of respective radiation sensors 18 or 36 which are respectively disposed close to the outlet of the photoreactor 1 or the top end of the outer irradiation chamber 35 provided that the optical conditions are met which are required therefore during irradiation. The radiation sensor 18 or 36 supplies an output signal which corresponds to the optical transmission of the medium. This output signal may be applied to indicating means indicating the optical transmission of the medium close to the end of its throughpassage through the respective irradiation chamber. The output signal may also be applied in a manner which is known as such, to control means controlling the pump which passes the medium to be irradiated through the photoreactor 1 or 21, as the case may be. Instead, the output signal may also be supplied to a power control such as known from European Patent No. 0,179,376, for controlling the power fed to the radiation source. In this manner, the throughflow and/or the radiative power of the radiation source can be adapted to particular purification requirements.

When operating the annular dual chamber throughflow photoreactor 21, the pump and/or the radiative power of the radiation source are advantageously controlled by the ouput signal of the radiation sensor 36 in a manner such that the decadic logarithmic absorbance close to the end of the outer irradiation chamber 35 assumes a value in the range of 0.20 to 0.40 which corresponds to an absorption range of 37% to 60% and a transmission range of 63% to 40%.

A further improvement in the oxidative photopurification can be achieved by sensitizing the photolysis of peroxi compounds, particularly hydrogen peroxide, using finely divided semiconducting metal compounds like titanium dioxide (commercially available from Degussa under the designation Pe 25). In addition to the UV-C range, titanium dioxide is also photochemically effective in the longer wavelength UV-A and UV-B ranges above 270 nm up to 400 nm in which absorption by hydrogen peroxide is insignificant. Thus, also the strong mercury emission lines at 280, 296,302,313,334 and 366 nm can be utilized for the oxidative photopurification. At a concentration of 50 mg/l, finely divided titanium dioxide causes radiation attenuation by scattering and absorption which are measured in 1 cm thickness as transmissions of 0.18 in the wavelength range below 300 nm and 0.20–0.30 in the wavelength range above 350 nm. It could be shown that an addition of titanium dioxide in the amount of 0.1 g/l to a saturated aqueous solution of tetrachloroethene containing hydrogen peroxide can improve the degradation by at least 30%. This effect is possibly assisted by an additional contribution due to UV scattering throughout the entire range. The solid titanium dioxide can be removed from the irradiated medium in known manner.

EXAMPLE 6

In the following Table III, constructional data are given of annular single chamber and dual chamber throughflow photoreactors used in combination with medium pressure mercury lamps. The dimensions given of the two types of photoreactors are matched to each other. The envelope tube 2 is absent in the photoreactors designated I and II whereas it is present in the photoreactors designated Ia and IIa.

The photoreactors are equipped with means for introducing gaseous oxygen. In the present constructions as well as in the others, infeed means for radical forming absorber may be provided at the inside of the outer irradiation chamber at least at one location along length of the passage path but at a multiple number of circumferential locations in order to continuously replenish the same or maintain a predetermined concentration of the radical forming absorber.

TABLE III

| Arc Length<br>Power Input | 170 cm<br>10.000 W | | 100 cm<br>5.880 W | |
|---|---|---|---|---|
| | I<br>cm | II<br>cm | Ia<br>cm | IIa<br>cm |
| Envelope Tube 2, | | | | |
| Outer Radius | | 3.0 | | 3.0 |
| Inner Tube 6, | | | | |
| Inner Radius | 8.0 | | 8.0 | |
| Spacer Tube 22, | | | | |
| Inner Radius | | 8.0 | | 8.0 |
| Separating Tube 23, | | | | |
| Inner Radius | | 9.7 | | 9.7 |
| Outer Radius | | 10.02 | | 10.02 |
| Inner Chamber 34, | | | | |
| Thickness | | 1.7 | | 1.7 |
| Volume, liter | | 9.45 | | 9.45 |
| Outer Steel Tube 7, | | | | |
| Inner Radius | 30.0 | | 30.0 | |
| Thickness | 22.0 | | 22.0 | |
| Outer Tube 28, | | | | |
| Inner Radius | | 40.02 | | 40.02 |
| Outer Chamber 35, | | | | |
| Thickness | | 30.0 | | 30.0 |
| Volume,Liter | | 471.6 | | 471.6 |
| Total Volume, Liter, at 1 m Arc Length, | 262.6 | 481,1 | 262.6 | 481.1 |

The space defined between the elongate radiation source and the respective transparent wall or spacer tube 6 or 22 or between the envelope tube 2 and the respective transparent wall or spacer tube 22 of the particular throughflow photoreactor is throughpassed by a flow of inert gas, for example, 3–10 lmin$^{-1}$ high purity nitrogen.

12% of the 10 kW power of the radiation source are delivered as UV radiation at a wavelength of 254 nm which corresponds to 9.17 mol quanta per hour; if all of this radiation is absorbed, then, at the quantum yield of 1 for the hydrogen peroxide decomposition, 9.17 mol or 311.7 g of hydrogen peroxide can be theoretically decomposed per hour. If a reaction has the quantum yield of 6 like, for example, the photooxidation of formaldehyde using hydrogen peroxide, then, the use of a 10 kW radiation source in the apparatus as given hereinbefore will require the uniform hourly supply of about 6·312 or 1,872 g of hydrogen peroxide. Theoretically this consumption of 1.87 kg of hydrogen peroxide would correspond to a COD degradation of 1.87/2.125=0.88 kg COD per hour. Note that the ratio of the oxidation equivalents of oxygen and hydrogen peroxide is 32/68 or 1/2.125.

A multiple number of single chamber type I-photoreactors according to TABLE III can be series-connected in order to achieve higher purification power. At the entry into the last stage, the UV transmittance of the irradiated medium may not exceed a value of 0.65 to 0.7 at a thickness of 1 cm. Preferably and at high purification requirements, the series of type I-photoreactors will be followed by one or more dual chamber type II-photoreactors according to TABLE III. In such arrangements, the radical forming absorber may be supplied intermediate the various photo-reactors and the medium may also be cooled, if desired.

In irradiation chambers in which radical forming absorber is supplied in distribution along the length of the irradiation chamber, particularly at thicknesses above about 7.5 cm, there may occur mixing problems during the throughflow. Such problems can be counteracted in different ways:

a) by introducing a finely divided gas flow which is introduced through fritted glass and which preferably contains oxygen;

b) by stirring, particularly using a known stirring device which is peripherally disposed and includes radially extending stirring paddles which have only a minimum effect on the radiation path;

c) by providing withdrawal means which are uniformly distributed along the periphery at different heights; such withdrawal means are connected via a circulating pump to a mixing chamber wherein further radical forming absorber is added and which is connected to the photoreactor through radial injection nozzles.

The introduction of gaseous oxygen into the medium under irradiation has further advantageous effects. When the oxidative photopurification is carried out solely using hydrogen peroxide, the photochemical disproportionation of hydrogen peroxide to yield water and oxygen, is the sole source of oxygen which, then, enters the different propagation reactions as indicated in II.b) of Table I hereinabove. In such reactions, the radicals which are formed in the starting reaction by the reaction of the starting radicals with the oxidizable carbon compound, react with oxygen to form highly reactive intermediates whereby the oxidative photopurification in its entirety is further advanced. The photochemical disproportionation of hydrogen peroxide, however, results in a loss of quanta with respect to the formation of hydroxyl radicals which initiate the oxidative photopurification. It has been found that this disproportionation reaction which results in the loss of quanta, can be competitively inhibited when oxygen is present in the medium under irradiation or when oxygen is continuously supplied to the medium in order to keep the medium saturated with oxygen, preferably at oxygen pressures up to 3 bar. According to experience, at least half of the stoichiometrically required hydrogen peroxide can be substituted by oxygen.

When the oxidative photopurification is carried out using a stoichiometrically required amount of 26 g of hydrogen peroxide per 100 Wh UV radiation at a wavelength of 254 nm, then, the following amounts of hydrogen peroxide and their corresponding oxygen equivalents will be reacted at different powers of the radiation source in Wh at 254 nm:

| Power of Radiation Source | 500 | 1,000 | 2,000 Wh |
|---|---|---|---|
| Amount of Hydrogen Peroxide | 130 | 260 | 520 g/h |
| Oxygen Equivalents | 61 | 122 | 245 g/h. |

Consequently, if oxygen is respectively supplied and reacted at a rate of about 30, 61 or 122 g/h, then, the amount of hydrogen peroxide to be added can be reduced to one half of the amounts given above. Part of the required hydrogen peroxide may also be introduced into the medium by supply means which are distributed along the length of the photoreactor.

For the aforementioned reasons and in principle, there is an advantage in introducing oxygen into the medium during irradiation. If desired, the oxygen may also be circulated through the medium under irradiation. Such oxygen circulation offers the possibility of simultaneously removing from the medium the carbon dioxide which is formed as a result of the oxidative photopurification. It is important therefore that the pH value of the medium can be maintained at pH 3 or below. This pH adjustment is important for achieving good quantum yields of the oxidative photopurification in view of the fact that the initiating hydroxyl radicals are subject to scavenging by carbonate or hydrocarbonate ions which are present in the aqueous medium at higher pH values and tend to react with hydroxyl radicals with the formation of radicals which have low oxidation potentials and thus will less probably enter the propagation reaction, see TABLE I, section IIc), Interfering Scavenging Reactions.

(Note: When subjecting cyanide or complex cyanide containing solutions to oxidative photopurification like, for example, waste water from galvanic installations or coking plants, the pH value must be maintained at pH 10 or higher in order to ensure that no hydrogen cyanide is released.)

In the Examples given further hereinabove, hydrogen peroxide and sodium persulphate have been employed as the radical forming absorber. Instead, and if desired, many other peroxi compounds such as peroxides, peroxi acids etc. may be used. Also, peroxides (ozonides) which are formed in the presence of ozone from the contaminants, may serve as radical forming absorbers.

The aforenoted photoreactions can be generally utilized for COD degradation in waste waters and leachates. Thus, the aforementioned 5.8 kW medium pressure mercury lamp supplies a photon flow of 600 Wh in the UV-C range and, at 254 nm, 130 Wh which corresponds to a quantum flow of 4.61 mol/h. Considering the quantum yield of 1 for the photolysis of hydrogen peroxide, this quantum flow will result in the photolysis of 4.61 mol/h of hydrogen peroxide which is the equivalent of 2.3 mol/h or 73.75 g/h of oxygen available for the degradation of 73.75 COD/h.

When the photochemical reactions in the UV-C range are restricted due to absorption by the contaminants, remedy is available by using finely distributed semiconductive metal compounds like, for example, titanium dioxide which is active up to wavelengths in the 400 nm range whereby the strong mercury lines at 280,296,302,313,334 and 366 nm can be additionally utilized for oxidative photopurification. The addition of sensitizers like titanium dioxide in the presence of oxygen has the added advantage that oxidative photopurification actions can also be initiated without the participation therein of hydrogen peroxide.

Furthermore, in the presence of oxygen even the long wavelength range may be made additionally accessible for oxidative photopurification if singlet oxygen producing sensitizers like, for example, eosin, rose bengal, porphins, or methylene blue are added. In particular, proteins and peptides may thus become photochemically degradable. The reaction products obtained thereby are, then, subject to further degradation by oxidative photopurification while also the sensitizers become degraded under the action of UV radiation and peroxides formed during these reactions.

A higher temperature may be very valuable for achieving increased quantum yields or prolonged reaction chains when carrying out the oxidative photopurification. Contrary to the addition of oxygen radicals to C=C double bonds, see the propagation reactions listed in section IIb) of TABLE I, the abstraction reactions listed in section IIa) of TABLE I, generally require some activation energy which becomes better available in the moderately increased temperature range of 30° C. to 90° C. than at the usual environmental temperatures. However, due to the compound mixtures which form the contaminants in the contaminated media, the usefulness of the operation at increased temperatures can not be readily predicted and must be pretested; there may also exist temperature optima.

Generally, at least one medium pressure mercury lamp having a rated power in the range of 10 W to 250 W per cm arc length is preferably employed and operated at a maximum power input in the range of 65% to 85% of the rated power for carrying out oxidative photopurification. Such radiation sources and others which are mentioned hereinbefore, produce considerable amounts of heat. For example, at a power input of 12 kWh, a medium pressure mercury lamp produces heat in an amount sufficient to heat 147 liters of water by 70° C. per hour (1 kW=3,600 kJ). Depending upon the thermal behavior of the particular medium which is subjected to oxidative photopurification, the heat generated by the radiation source thus may be used for heating the medium in order to thereby increase the quantum yield and chain length of the reaction where appropriate. If the process is favored by higher temperatures, it may be preferable to circulate the medium through the photoreactor or the first photoreactor of a series of series-connected photoreactors until the desired temperature is attained. However, the medium may also be passed through a preheating chamber prior to introduction into the photoreactor. In other cases, it may be desirable to cool the medium during irradiation. In such event, the or each photoreactor can be provided with cooling means or, in the alternative, a cooling device may be provided through which the medium is passed by circulation, if only a single photoreactor is used, or through a cooling device which is arranged between the photoreactors in a series of series-connected photo-reactors.

Figure 3:
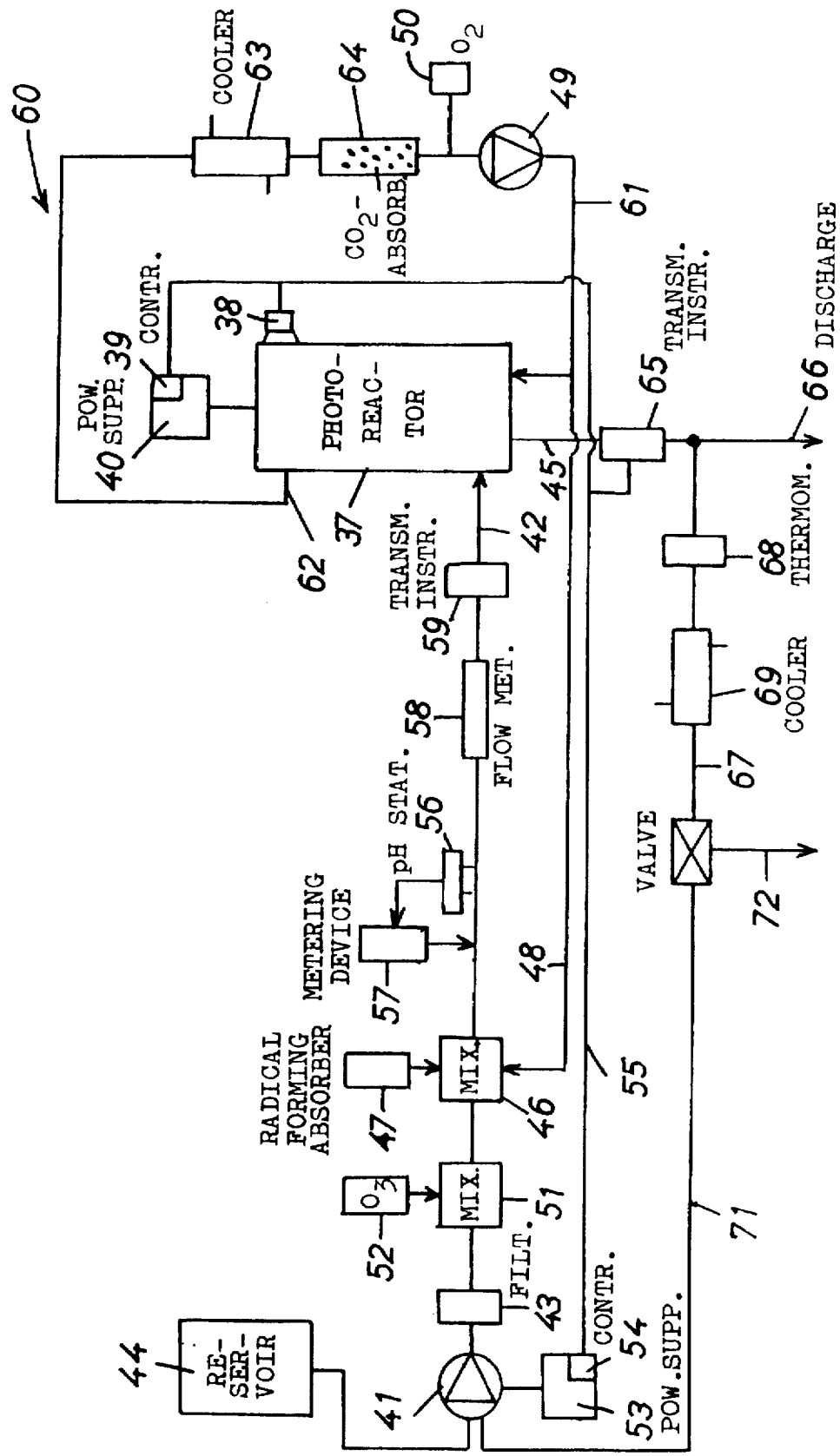
FIG. 3 is a schematic illustration in the form of a block circuit diagram showing an apparatus for carrying out the inventive method using a throughflow photoreactor as shown in FIG. 1 or FIG. 2.

FIG. 3 is a schematic, summarizing illustration showing the various possible modes of carrying out the oxidative photopurification of an optically transparent medium. Therein, the annular throughflow photoreactor is designated by reference numeral 37 and may be constructed in the manner as shown in FIG. 1 or 2. In the case of an annular dual chamber throughflow photoreactor as shown in FIG. 2, a UV sensor 38 is provided on the outside near the outlet of its outer irradiation chamber. The UV sensor 38 is connected to a control section 39 of a power supply 40 for the radiation source in order to enable the radiation power to be adapted to particular requirements. The medium to be irradiated is passed through a filter 43 to an inlet 42 of the photoreactor 37 by means of a pump 41 having an input which is selectively connectable either to a reservoir 44 or, in the event of circulation, to an outlet 45 of the photoreactor 37. A conventional mixing device 46 is located between the pump 41 and the inlet 42. Therein, radical forming absorber is added to the medium to be irradiated from supply means 47 which also may serve to add thereto further ingredients like sensitizers. The supply means 47 is conventionally constructed and includes a reservoir which is connected to the mixing chamber 46 through a controlled metering pump and valve means.

The mixing chamber 46 is connected to an oxygen infeed conduit or line 48 for oxygen. The conduit or line 38 is connected to an oxygen source 50 through a pump 49 in order to enable saturating the medium to be irradiated with oxygen at a desired pressure in the range of, for example, 1 to 3 bar.

If desired, an oxidizing chamber 51 may be arranged preceding the mixing chamber 46, as viewed in the flow direction. The oxidizing chamber 51 is connected to an ozone generator 52 which may also be connected to the oxygen conduit or line 48.

The pump 41 is operated by means of a power supply 53 including a control section 54 which is connectable to the UV sensor 38 via a line or conductor 55 in the event that it is intended to control the throughflow through the photoreactor 37 instead of, or additionally to, the power of the radiation source.

The mixing chamber 46 is followed in flow direction by pH measuring and regulating means including a conventional pH stat 56 controlling a conventional metering means 57 for pH adjustment, a flow meter 58, and a transmission measuring instrument 59 having an output which is connected to the photoreactor inlet 42. The instrument 59 preferably is connected in parallel to the inlet 42.

The photoreactor 37 may be connected to oxygen circulation means 60 including the pump 49 having an output which is connected to an infeed conduit or line 61 from which the gas is introduced into the photoreactor 37 through one or more fritted glass inputs. The pump 49 is connected on the input side to an outfeed 62 which issues from the photoreactor 37 and contains a splash guard. The circuit may contain a cooler 63 and an absorber 64 for carbon dioxide.

The purification product issues from the photoreactor 37 through the outlet 45. A further transmission measuring instrument 65 is shunted to the outlet 45 through a liquid filter (not illustrated). The output signal of the instrument 65 is connected to the control section 54 of the power supply 53 for the pump 41 as well as to the control section 39 of the power supply 40 for the radiation source via a line or conductor 55. The output signal of the transmission measuring instrument 65, then, can be used instead that from the UV sensor 38 for the aforenoted control purposes. In the event that the purification product has sufficient purity, it may be removed by means of the discharge 66. In the case that further purification is required, the outlet 45 is connected to a conduit or line 67 which, if desired, is provided with a thermometer 68 and a cooler 69 and terminates in a switch valve which may be constructed as a 3-way valve. The aforementioned pH adjusting means 56,57 may be incorporated also or instead into the conduit or line 67. One output of the switch valve is connected to the pump 41 through a conduit or line 71 in order to thereby operate the photoreactor 37 in circulation. In the event that the apparatus shown in FIG. 3 represents one photopurification stage in a plural number of series connected photopurification stages, a further output of the switch valve may lead to a further purification stage through a conduit or line 72 which is protected from backflow.

For control purposes, the arrangement according to FIG. 3 may still be provided with a number of sampling and temperature measuring locations which are conventionally constructed and connected thereto in conventional manner and, therefore, not particularly indicated.

The photoreactor 37 is schematically shown in FIG. 3 in connection with its various supply and control means. It will be understood that the arrangement of the various supply and control means is dependent upon the construction of the particularly employed photoreactor and adapted to further requirements concerning, for example, the laying of conduits and conductors, available space etc. For instance, when using photoreactors like those shown in FIGS. 1 and 2, the mixing chamber 46 may be located close to the photoreactor or may even be formed integrally therewith whereby the different supply conduits or lines will directly lead into such mixing chamber.

Figure 4:
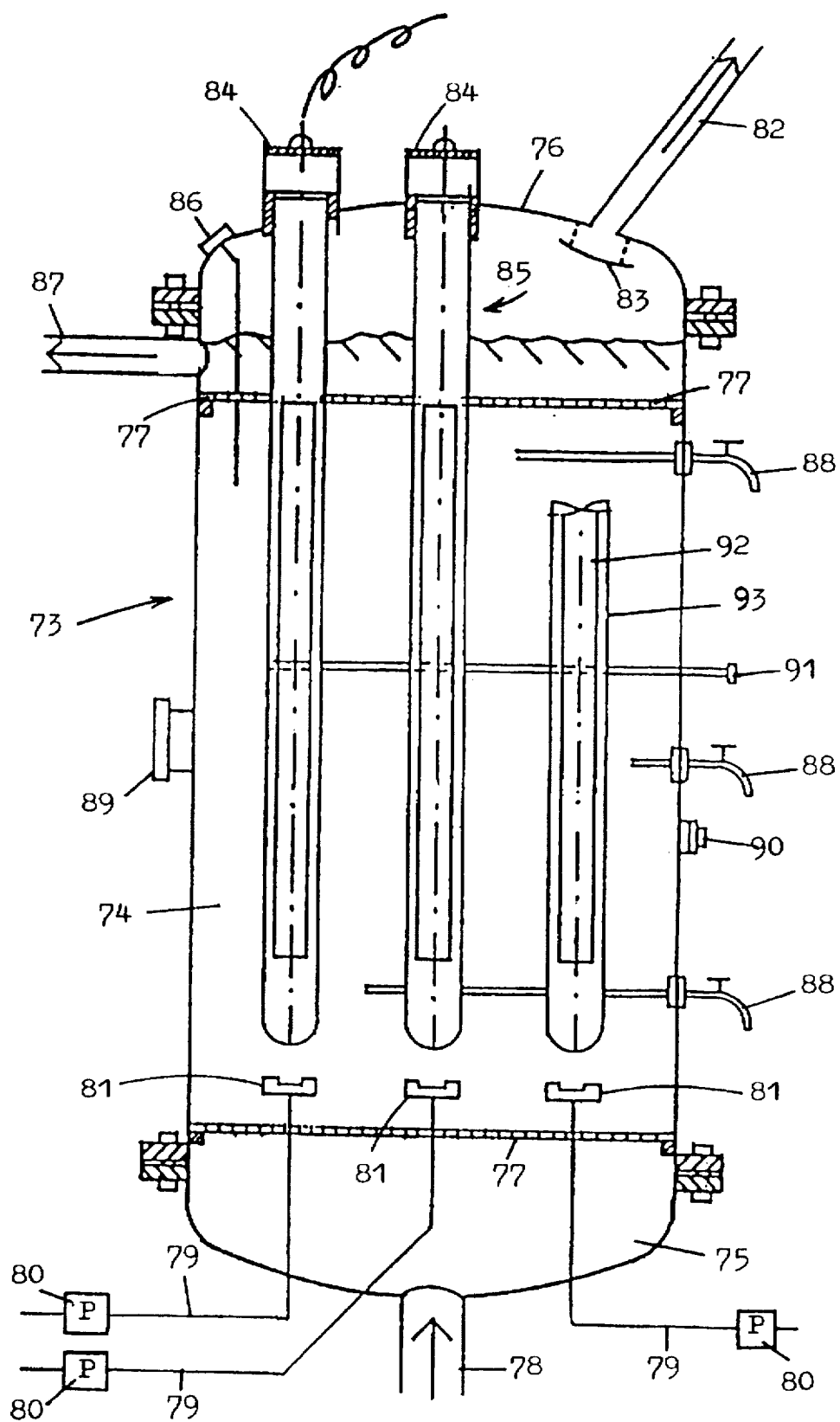
FIG. 4 is a schematic longitudinal section through a third exemplary embodiment of the invention in the form of a tank reactor.

A third exemplary embodiment of the invention will now be described with reference to FIGS. 4 to 6. FIG. 4 shows a longitudinal section through a throughflow photoreactor in the form of a generally cylindrical, substantially vertically disposed tank reactor 73. In the illustrated embodiment, the tank reactor 73 comprises a substantially cylindrical midportion 74, a lower end portion 75, and a top end portion 76 wherein the end portions 75 and 76 are pressure-tightly connected to the midportion 74 by means of conventional flange connections. The tank reactor 73 constitutes a pressure resistant container for the throughflowing medium to be irradiated and may be made of, for example, glass, ceramic material, enamelled steel, stainless steel or plastic. The midportion 74 is provided close to both its ends with means for equalizing the flow of the throughflowing medium to be irradiated; in the illustrated exemplary embodiment, such means 77 is formed by perforated plates.

The lower end portion 75 is provided with an inlet 78 for the medium to be irradiated. Gas supply lines or conduits 79 are sealingly passed through the end portion 75. Each one of the gas supply lines or conduits 79 includes a gas feed pump 80, preferably a diaphragm pump, and extends through the associated perforated plate. The gas supply lines or conduits 79 terminate in respective gas infeed means 81 which preferably constitute fine-pore frits.

The top end portion 76 includes a gas outlet 82 provided with a conventional splash guard 83 arranged within the top end portion 76. Furthermore, retaining and connecting means 84 for each one of a plurality of irradiation units 85 and a temperature measuring device 86 are sealingly inserted through the top end portion 76. The irradiation units 85 and the temperature measuring device 86 extend through the upper perforated plate into the interior of the midportion 74. Preferably, the retaining and connecting means 84 constitute integral parts of the irradiation units 85.

The midportion 74 further includes a product outlet 87 for irradiated medium close to its upper end and sampling means 88 which are distributed along the length of the midportion 74 and which protrude to different depths into the interior of the midportion 74. Furthermore, a viewing glass 89 for observation purposes and one or more UV sensors 90 for monitoring the irradiation units 85 are attached to the midportion 74. Finally, infeed means 91 is provided at the tank reactor 73 for infeeding radical forming absorber during the irradiation and throughflow of the medium to be irradiated. The infeed means 91 extends along the circumference of the midportion 74 and include conventionally constructed injection nozzles (not illustrated) by means of which radical forming absorber is injected into the medium. In the illustrated exemplary embodiment only one such infeed means 91 is provided and arranged at the longitudinal center of the midportion 74. If desired, a plural number of such infeed means 91 can be provided and distributed along the length of the midportion 91.

Irradiation is effected by means of a plural number of irradiation units 85 which are connected to external power supply means present in a control cabinet (not illustrated) of the usual type. Each such irradiation unit 85 includes an elongate radiation source 92 which is coaxially surrounded by a transparent wall in the form of a spacer tube 93 which is closed at its bottom end. Additionally, the radiation source 92 may be surrounded by a conventional envelope tube having a maximum diameter of 6 cm. The radiation source 92 extends along most of the length of the midportion 74. The closed end of the spacer tube 93 is located closely above the associated gas infeed means 81. As a result, a current of finely divided gas bubbles rising from the gas infeed means 81 runs essentially along the respective spacer tube 93 and thereby effects thorough mixing of the throughflowing medium and a layer of the medium which immediately adjoins the respective spacer tube 93 and which layer receives the incident radiation.

Figure 5:
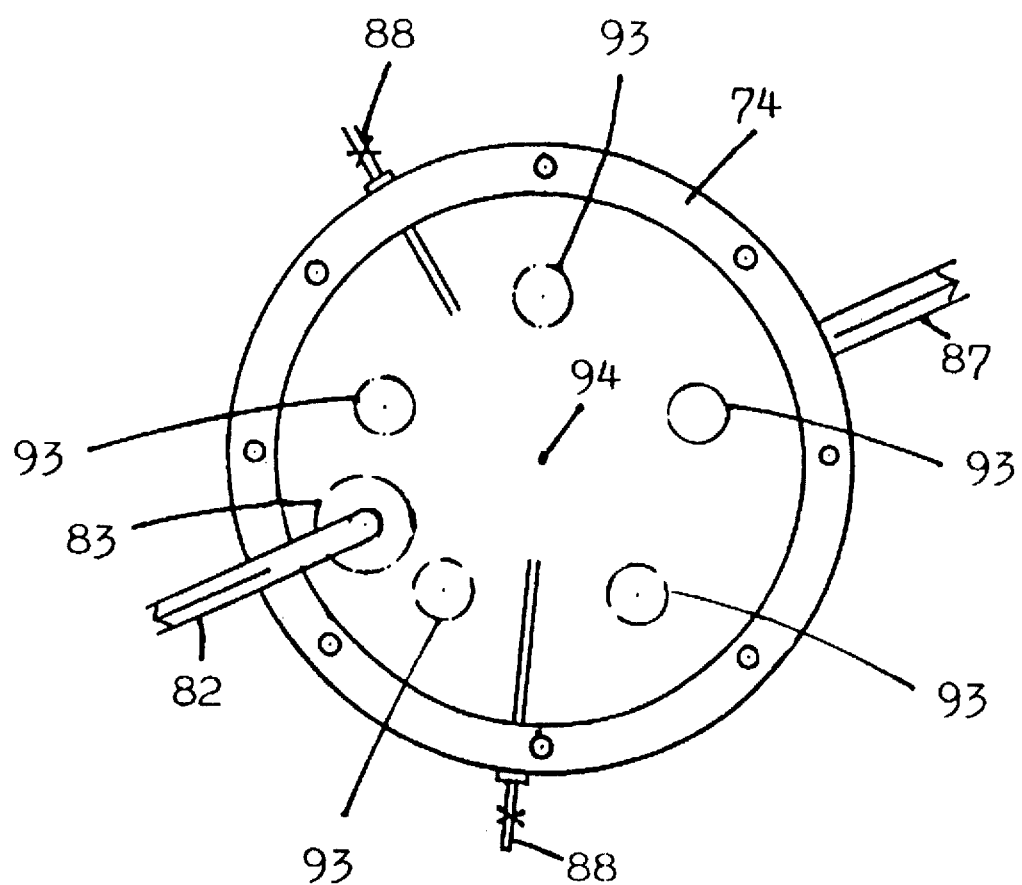
FIG. 5 is a schematic cross-section through the tank reactor as shown in FIG. 4.

As will be evident with reference to the cross-section of the tank reactor 73 shown in FIG. 5, the irradiation units 85 are arranged in an annular array disposed around the central longitudinal axis 94 of the tank reactor 73 and extend substantially parallel to such axis 94. In the illustrated exemplary embodiment, five irradiation units 85 are arranged at equal mutual spacings between the central longitudinal axis 94 and the inner wall of the midportion 74. If required, an additional irradiation unit 85 may be arranged to extend along the central longitudinal axis 94. The number and arrangement of the irradiation units 85 as well as their mutual spacing is a function of the radiation power required for a particular oxidative photopurification.

Each irradiation unit 85 is constructed as explained hereinbefore while taking account of the initially discussed square root dependency of the photochemical radical formation on the irradiance. Each such unit 85 includes an elongate radiation source 92 which preferably constitutes a medium pressure mercury lamp or arc having a rated power in the range of 10 to 250 W/cm of arc length, which is selected in accordance with the particular irradiation requirements, and which is operated at a maximum power input in the range of 65% to 85% of the rated power. The transparent wall or spacer tube 93, which is made of quartz glass, surrounds the elongate radiation source 92 at a radial spacing of more than 3 cm from the lengthwise axis of the elongate radiation source. The radial spacing preferably is in the range of more than 3 cm up to 13 cm, the range of 4 cm to 9 cm being most preferred. The following TABLE IV shows the dimensions of selected transparent walls or spacer tubes 93.

TABLE IV

| Dimensions of Selected Spacer Tubes | | | |
|---|---|---|---|
| Radius, cm | 8.0 | 7.5 | 7.0 |
| Length, cm | 100 | 100 | 100 |
| Volume, liter per meter | 20.11 | 17.67 | 15.39 |
| Irradiation area cm² per meter | 5026.55 | 4712.39 | 4398.23 |

In the following TABLE V, data are given for different tank reactors 73 which contain different numbers of annularly arranged irradiation units 85 with respective transparent walls or spacer tubes 93 having a radius of 8 cm.

TABLE V

Data of Selected Tank Reactors Having Different Numbers of Irradiation Units
(Length: 100 cm; Spacer Tube Radius: 8 cm)

| | Spacer Tube Number | | |
|---|---|---|---|
| | 5 | 6 | 18 |
| Radius, cm | 31.00 | 31.00 | 55.00 |
| Spacer Tube Array Radius, cm | 20.00 | 20.00 | 43.00 |
| Single Spacer Tube Volume, liter | 40.28 | 30.21 | 32.70 |

TABLE V-continued

Data of Selected Tank Reactors Having Different Numbers of Irradiation Units
(Length: 100 cm; Spacer Tube Radius: 8 cm)

| | Spacer Tube Number | | |
|---|---|---|---|
| | 5 | 6 | 18 |
| Gross Tank Volume, liter | 301.91 | 301.91 | 950.33 |
| Net Tank Volume, liter | 201.38 | 181.27 | 588.42 |
| Throughflow at 1 m/sec, m³/h | 724.97 | 652.57 | 2,118.31 |

Figure 6:
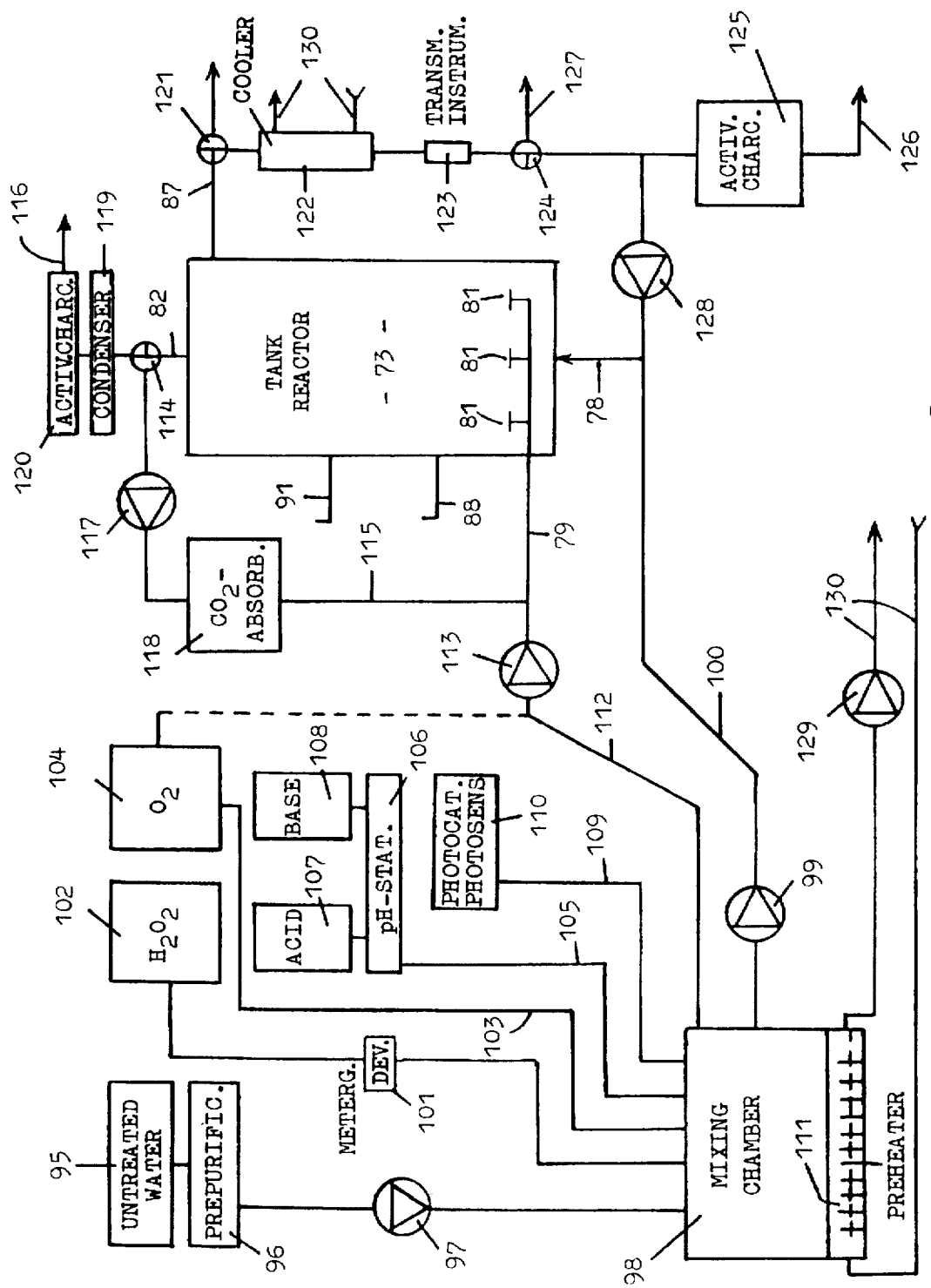
FIG. 6 is a schematic illustration in the form of a block circuit diagram showing an apparatus for carrying out the inventive method using the tank reactor as shown in FIGS. 4 and 5.

FIG. 6 is a schematic block diagram of an installation for oxidative photopurification similar to FIG. 3 and including a tank reactor 73 as described hereinbefore with reference to FIGS. 4 and 5. Such installation serves for the oxidative photopurification of the most various types of untreated water. The oxidative photopurification may represent an individual stage of a manufacturing process in which the purified water is recycled into the manufacturing process. However, the oxidative photopurification may also constitute the final step in a purification process. For economical reasons, there is frequently provided a combination of different method steps in which an activated charcoal treatment in the final step has been found to be of greatest interest. Purification costs tend to significantly increase with decreasing contaminant concentration. It is for this reason that in many cases only partial contaminant degradation is considered desirable in the treatment of, for example, leakage water from waste dumps.

The detailed equipment employed in an installation for oxidative photopurification is particularly determined by the absorption of the medium to be irradiated in the wavelength range of 200 nm to 280 nm as well as by the COD-value of such medium. The radical forming absorber will be added in an amount which will result in a sufficient proportional amount of the incident radiation even at high absorption of the medium. The choice of the amount of radical forming absorber as well as the constructional details of the irradiation equipment such as the dimension of the spacer tube, the rated power of the radiation sources and the number of radiation sources will depend upon the particularities of the medium to be irradiated and upon economic considerations. An example will be given hereinbelow following the description of such installation.

In FIG. 6, there will be recognized the tank reactor 73 including the inlet 78 and the gas supply line or conduit 79 provided with the gas infeed means 81 as well as the gas outlet 82, the product outlet 87, the sampling device 88 and the infeed means 91 for supplementing the radical forming absorber during irradiation.

The untreated water to be irradiated is supplied to a mixing chamber 98 by means of a first feed pump 97 from an untreated water source 95 via a conventional prepurification stage 96 for removing coarse and/or non-aqueous contaminants. The mixing chamber 98 is connected to the inlet 78 of the tank reactor 73 through a further or second feed pump 99 and a feed line or conduit 100. Furthermore, the mixing chamber 98 is connected through a metering device 101 to a reservoir 102 containing radical forming absorber, for example, an aqueous hydrogen peroxide solution, as well as to a source 104 of pressurized oxygen through an oxygen supply line or conduit 103. The oxygen is introduced into the medium in known manner with the aid of gas frits or gas injectors. Furthermore, the mixing chamber 98 is connected via an infeed line or conduit 105 to pH measuring and regulating means or pH stat 106 which supplies, depending upon the prevailing conditions, an acid or basic neutralisation agent from respective reservoirs 107 and 108 to the mixing chamber 98. Such measuring and regulating means are known in the art of pH control and, therefore, do not require more detained description. Finally, a further feed line or conduit 109 may be provided and extends from a reservoir 110 for supplying photocatalyst or photosensitizer to the mixing chamber 98. A preheater 111 is installed in the mixing chamber 98 for preheating the medium to be irradiated to a temperature higher than the environmental temperature whereby the degradation reactions are favored in the untreated water containing the various ingredients during irradiation in the tank reactor 73.

An oxygen line or conduit 112 extends from the mixing chamber 98 to take up non-dissolved oxygen; the oxygen line or conduit 112 is provided with an oxygen feed pump 113. The gas supply lines or conduits 79 which lead to the gas infeed means 81 disposed within the tank reactor 73, branch off from the oxygen line or conduit 112 downstream of the oxygen feed pump 113. As indicated by the broken line, the input side of the oxygen feed pump 113 may also be directly connected to the pressurized oxygen source 104. The gas outlet 82 of the tank reactor 73 can be selectively connected to either a gas recirculation 115 or a gas discharge 116 via a gas switch valve 114. The gas recirculation 115 includes a circulation pump 117 which is connected to the oxygen line or conduit 112 downstream of the oxygen feed pump 113 through a carbon dioxide absorber 118. In this manner, the purified oxygen is recycled into the tank reactor 73. When the pH of the untreated water is adjusted to a value of pH 3, scavenging reactions of carbonate and bicarbonate ions with the hydroxyl radicals are avoided which otherwise would detrimentally affect the efficiency of the propagation reactions, see section IIc. in Table I hereinabove.

In the event that the recovery of carbon dioxide from the oxidative photopurification is uneconomic, use of the recirculation 115 or even the recirculation 115 itself may be dispensed with. The used gas is then vented to the atmosphere via the gas discharge 116 as shown by the illustrated position of the gas switch valve 114 in which position the used gas passes through a condenser 119 and a filter 120 which preferably is an activated charcoal filter. The still contaminated condensate accumulating in the condenser 119, will be returned to the tank reactor 73.

The medium which exits from the product outlet 87 of the tank reactor 73 and which is purified by oxidative photopurification, has been considerably heated as a result of the irradiation. As already explained hereinbefore, in fact, only about 16% of the electrical energy consumed by the radiation sources 92 is converted into effective radiative energy while a much greater portion of the supplied electrical energy is converted into heat. Therefore, the product medium is selectively passed by means of a first switch valve 121 to either a cooler 122 (as illustrated) or a further throughflow photoreactor or its mixing chamber. Subsequent to the cooler 121, the product medium is passed through a throughflow optical transmission measuring instrument 123 for control purposes. The output signal of the transmission measuring instrument 123 may be utilized, for example, to control the power supplied to the irradiation units 85 or the second feed pump 99.

In the illustrated exemplary embodiment, the product issuing from the transmission measuring instrument 123 is selectively passed by means of a second switch valve 124 to either an activated charcoal stage 125 and a product discharge 126 (as illustrated) or a direct discharge 127. The activated charcoal stage 125 serves the purpose of removing non-reacted hydrogen peroxide. If the product can be further used immediately, it may be directly passed to the direct discharge 127 through the correspondingly adjusted second switch valve 124.

Expediently, a further circulation pump 128 is provided on an output side of the second switch valve 124. The further circulation pump 128 is connected to the inlet 78 of the tank reactor 73 and permits the untreated water, to which various ingredients have been added, to be circulated during the run-in phase of the operation of the radiation sources 92. If desired, part of the medium to be irradiated may thereby also be circulated during the actual irradiation; the further or second feed pump 99 will, then, be operated at correspondingly reduced power.

The coolant for the cooler 122 at the product outlet 87 of the tank reactor 73 advantageously is circulated by means of a third circulation pump 129 and a coolant circulation 130 which includes the preheater 111 present in the mixing chamber 98.

EXAMPLE 7

In this example, there will be described the oxidative photopurification of a biologically pre-purified leakage water from a waste dump in the aforedescribed installation. The biologically pre-purified leakage water from the waste dump had the following data:

Yellowish liquid; absorbance 2.45 $cm^{-1}$ or transmission of 0.00355 at a wavelength of 254 nm and a thickness of 1 cm;

COD-value: 1.9 $kg/m^3$, and thereof

AOX (Adsorbable Organic Halogen Compounds): 1.50 $g/m^3$.

The data of the oxidative photopurification installation were as follows:

Inner tank reactor radius: 31 cm;

5 irradiation units 85 in annular array, radial spacing from central longitudinal axis 94: 20 cm;

spacer tube radius: 7 cm;

spacer tube length: 150 cm;

mutual spacing in annular array: 9.5 cm;

spacing from tank reactor inner wall: 4 cm;

1 irradiation unit along the central longitudinal axis 94, radial spacing from annular array: 6 cm;

6 medium pressure mercury lamps 92 each having a rated power of 15 kW, total of 90 kW;

incident UV radiation (computed for 254 nm): 1.5 UV-kW for each lamp 92 or a total of 9 UV-kW, corresponding to 68.76 mole photons at the wavelength of 254 nm;

arc length: 150 cm;

spacer tube volume: 23.10 liter each, a total of 138.54 liter;

gross tank reactor volume: 452.86 liter;

net tank reactor volume: 314.32 liter;

throughflow: 754.37 $m^3/h$ at 1 m/sec linear flow rate; and residence time: 754.37 seconds or 12.57 minutes at 1 m/sec linear flow rate.

The untreated water is adjusted to pH 3 in the mixing chamber 98 and hydrogen peroxide is added thereto in the amount of 2.8 kg per $m^3$. Under these conditions, the absorbance at 254 nm is 4.015 $cm^{-1}$. This implies that 90% of the incident radiation is absorbed in a layer having a thickness of 0.25 cm and that 39% of the incident photons will be absorbed by hydrogen peroxide. Oxygen is supplied to the mixing chamber 98 in an amount of 3 kg/m$^3$; the not dissolved oxygen is infed into the tank reactor 73 through the oxygen line or conduit 112 and the gas supply lines or conduits 79. The remaining gas is discharged to the atmosphere through the gas discharge 116 after passing through the condenser 119 and the activated charcoal filter 120.

1 kg COD, i.e. a chemical oxygen demand of 1 kg corresponds to a stoichiometrical amount of 2.125 kg hydrogen peroxide (1 mole hydrogen peroxide provides 1 gramatom of oxygen). Correspondingly, 4.037 kg/m$^3$ hydrogen peroxide will be required for 1.9 kg/m$^3$ COD. The added amount of 2.8 kg/m3 of hydrogen peroxide thus is the equivalent of 70% of the theoretically required amount.

At a throughflow rate of 4.5 m$^3$/h, the COD value of the product issuing from either one of the product outlets 126 or 127 of the tank reactor 73 of the present example, amounts to 0.7 kg/m$^3$; the AOX components were degraded completely. Consequently, 1.2 kg/m$^3$ COD has been degraded or a total of 4.5·1.2=5.4 kg COD at a total electric energy consumption of 90 kWh which corresponds to 16.7 kWh per kg degraded COD.

Residual hydrogen peroxide was removed in the activated charcoal stage 125 preceding the product discharge 126. The product has been heated by 17° C. in comparison to the temperature of the untreated water entering the tank reactor 73. The coolant flowing through the coolant circulation 130 thus heats the medium to be irradiated which is present in the mixing chamber 98, to temperatures above 30° C. which favorably affects the radical chain reactions proceeding during the COD degradation in the tank reactor 73.

For achieving higher throughputs, it is recommended that the tank reactor 73 is provided with a greater inner radius of, for example, 51 cm and an annular array of 18 irradiation units 85 as well as one centrally disposed irradiation unit 85. Under otherwise unchanged conditions, the net volume amounts to 787 liter; the same COD degradation of 1.2 kg/m$^3$ as in the presently described example will be achieved at a throughput of 14.25 m$^3$/h.

Still higher degradation rates can be attained upon working at increased oxygen pressures up to 3 bar. For achieving higher purification, a plural number of the aforedescribed tank reactors 73 can be series-connected. However, in the event that very high purification degrees are required, the absorbance in the final purification stage of the series will be very low. Then, an annular dual chamber throughflow photoreactor of the type as described hereinbefore with reference to FIG. 2 of the drawings will be preferably employed in the final stage of the oxidative photopurification.

The range of application of the aforedescribed methods and photoreactors is quite wide and not at all limited to the mineralization of the chlorinated hydrocarbons or dump leachates specifically mentioned in the Examples. Further potential examples concern rinsing and other waste waters originating from the beverage producing and bottling industry, slaughter houses, dry cleaning installations, hospitals, leather and gelatin producing and processing plants, paper and cellulose producing and processing plants following chemical bleaching operations, ammunition factories, nitro compound containing waste waters from dye producing and dyeing installations, PCB containing waste waters, waste waters containing motor fuel and petrochemical products, wetting agent containing waste waters from, for example, flotation installations, cyanide containing waste waters from galvanic installations, waste waters originating from coking plants and blast furnaces and many others.

Due to its environmentally favorable nature, the oxidative photopurification using the combination of UV irradiation and peroxides like hydrogen peroxide and/or ozone, has become highly important. The wide-range application hitherto has been prevented by the high costs involved therewith. Most of the presently practiced photoreactors also including photodisinfection of potable water as well as waste water, are operated on the basis of a linear dependency of photon requirements, i.e. according to the aforementioned Bunsen-Roscoe Law. Accordingly, the photochemical conversion achieved increases or decreases linearly with the irradiation intensity and the quantum yield is independent of the irradition intensity. This is particularly evident, for example, from the ideal characteristic of the dose-effect relationship observed in the UV inactivation of bacteria.

Contrary thereto, the quantum yields and the extent of conversion in the oxidative photopurification which proceeds via intermediate radical reactions, regularly depend upon the square root of the irradiation intensity and the square root of the concentration of the radical forming absorber but directly upon the oxygen concentration. By adequately considering and taking into acount these relationships when utilizing the herein described methods and apparatuses for oxidative photopurification, the energy consumption and the irradiation costs and others like investment and operating costs can be significantly decreased such as by at least 50% in comparison to the prior art.

While there are shown and described present preferred embodiments of the invention, it is to be distinctly understood that the invention is not limited thereto, but may be otherwise variously embodied and practiced within the scope of the following claims. Accordingly,

What I claim is:

1. An apparatus for oxidative photopurification of an optically transparent medium contaminated by at least one oxidizable carbon compound, said apparatus comprising:

an elongate radiation source defining a lengthwise axis and emitting radiation including UV radiation in the wavelength range below 280 nm during operation;

said elongate radiation source comprises at least one medium pressure mercury lamp;

an annular reaction chamber coaxially surrounding said at least one medium pressure mercury lamp for receiving an optically transparent medium contaminated by at least one oxidizable carbon compound and containing a dissolved radical forming absorber which forms two free radicals upon photolysis by said UV radiation in the wavelength range below 280 nm emitted by said at least one medium pressure mercury lamp, each one of said two free radicals being capable of initiating a sequence of oxidizing radical reactions by reacting with said at least one oxidizable carbon compound;

a transparent wall, which is made of quartz glass and transparent for said UV radiation in the wavelength range below 280 nm emitted by said at least one medium pressure mercury lamp, for passing said UV radiation into said medium present in said reaction chamber; and said transparent wall made of quartz glass surrounding said at least one medium pressure mercury lamp at a radial spacing of more than 3 cm from said lengthwise axis of said at least one medium pressure mercury lamp.

2. The apparatus as defined in claim 1, wherein said transparent wall is disposed at a radial spacing in the range of more than 3 cm to 13 cm from said lengthwise axis of said at least one medium pressure mercury lamp.

3. The apparatus as defined in claim 2, wherein said transparent wall is disposed at a radial spacing in the range of 4 cm to 9 cm from said lengthwise axis of said at least one medium pressure mercury lamp.

4. The apparatus as defined in claim 1, further including an envelope tube surrounding said at least one medium pressure mercury lamp at a maximum radial spacing of 3 cm from said lengthwise axis of said at least one medium pressure mercury lamp.

5. The apparatus as defined in claim 1, further including means for selectively passing either (i) an optically transparent protective gas or (ii) an optically transparent cooling fluid through the space formed between said at least one medium pressure mercury lamp and said transparent wall.

6. The apparatus as defined in claim 1, wherein said reaction chamber and said transparent wall are dimensioned such that the highest possible amount of the incident radiation is absorbed in said reaction chamber at the lowest possible irradiance, i.e. radiant flux per area of said transparent wall.

7. The apparatus as defined in claim 1, wherein:
said at least one medium pressure mercury lamp having a rated power in the range of 10 W to 250 W per cm arc length for operation at a maximum power input in the range of 65% to 85% of the rated power.

8. The apparatus as defined in claim 1, further including:
supply means for supplying radical forming absorber to said medium to be irradiated in said reaction chamber;
said supply means including a mixing chamber connected to an inlet side of said reaction chamber; and
a reservoir containing radical forming absorber and connected to said mixing chamber.

9. The apparatus as defined in claim 8, further including a metering device interconnecting said reservoir and said mixing chamber.

10. The apparatus as defined in claim 8, further including:
infeed means for infeeding radical forming absorber into said medium present in said reaction chamber;
said infeed means being disposed at least at one location along the length on the inner side of said reaction chamber.

11. The apparatus as defined in claim 10, wherein said infeed means disposed at said at least one location along the length of said inner side of said reaction chamber extends around the circumference on the inner side of said reaction chamber for introducing said radical forming absorber at a plural number of places distributed around said circumference.

12. The apparatus as defined in claim 8, further including oxygen supply means connecting an oxygen source and said mixing chamber for saturating said medium with oxygen under a pressure in the range of 1 to 3 bar.

13. The apparatus as defined in claim 12, further including:
pH measuring and regulating means including acidic and basic agent reservoirs for adjusting the pH of the medium to a value of pH 3; and
said pH measuring and regulating means being selectively connected to either (i) said mixing chamber or (ii) a feed line interconnecting said mixing chamber and said inlet side of said reaction chamber.

14. The apparatus as defined in claim 12, further including:
gas recirculation means;
a gas outlet provided at said reaction chamber;
an oxygen infeed conduit selectively connecting either (i) said oxygen source or (ii) said mixing chamber to said reaction chamber; and
said gas recirculation means comprising a circulation pump having an input side connected to said gas outlet of said reaction chamber and an output side connected to said oxygen infeed conduit.

15. The apparatus as defined in claim 14, wherein said gas recirculation means further comprises a carbon dioxide absorber connected between said gas outlet of said reaction chamber and said input side of said circulation pump.

16. The apparatus as defined in claim 15, further including a cooler interconnected between said carbon dioxide absorber and said gas outlet of said reaction chamber.

17. The apparatus as defined in claim 14, further including:
a gas discharge connected to a condenser through a filter; and
a switch valve connected to said gas outlet of said reaction chamber and selectively connecting said gas outlet either (i) to said gas recirculation means or (ii) through said condenser and said filter to said gas discharge.

18. The apparatus as defined in claim 8, further including:
an ozone generator producing an ozone/oxygen mixture;
an oxidizing chamber preceding said mixing chamber and receiving said medium contaminated by said at least one oxidizable carbon compound; and
said ozone generator being connected to said oxidizing chamber.

19. The apparatus as defined in claim 1, wherein said reaction chamber constitutes at least one throughflow photoreactor for throughpassing said medium to be irradiated.

20. The apparatus as defined in claim 19, wherein:
said at least one throughflow photoreactor comprises a plural number of series connected throughflow photoreactors; and
cooling means are selectively provided either (i) at least at one of said plural number of series connected throughflow photoreactors or (ii) at least between two consecutive ones of said plural number of series connected throughflow photoreactors.

21. The apparatus as defined in claim 19, wherein:
said at least one throughflow photoreactor comprises a plural number of series connected throughflow photoreactors; and
means for selectively adding said radical forming absorber to said medium to either (i) at least one of said plural number of series connected throughflow photoreactors or (ii) at least between two consecutive ones of said plural number of series connected throughflow photoreactors.

22. The apparatus as defined in claim 19, wherein said at least one throughflow photoreactor constitutes a substantially vertically disposed, annular throughflow photoreactor incorporating said transparent wall made of quartz glass on the side facing said at least one medium pressure mercury lamp.

23. The apparatus as defined in claim 22, wherein said annular throughflow photoreactor is an annular single chamber photoreactor.

24. The apparatus as defined in claim 22, wherein:
said annular throughflow photoreactor is an annular dual chamber throughflow photoreactor;
said annular dual chamber throughflow photoreactor including an inner irradiation chamber facing said at least one medium pressure mercury lamp and an outer irradiation chamber disposed remote from said at least one medium pressure mercury lamp;

said outer irradiation chamber being provided with inlet means for infeeding said medium into said annular dual chamber throughflow photoreactor and overflow means for passing said medium into said inner irradiation chamber; and a pump connected to said inlet means for passing said medium through said outer irradiation chamber and said inner irradiation chamber in countercurrent fashion.

25. The apparatus as defined in claim 24, wherein said outer radiation chamber and said inner irradiation chamber have thicknesses in a ratio in the range of (3 to 40):1.

26. The apparatus as defined in claim 19, further including control means for controlling the throughflow through said at least one throughflow photoreactor.

27. The apparatus as defined in claim 26, further including:

a pump for throughpassing said medium through said at least one throughflow photoreactor;

said pump having a power supply and a control section in said power supply;

said at least one medium pressure mercury lamp being connected to a power supply having a control section;

transmission measuring means associated with said at least one throughflow photoreactor for measuring the optical transmission of said medium selectively either (i) during irradiation or (ii) after irradiation; and said transmission measuring means being selectively connected to either (i) said control section of said power supply supplying power to said pump or (ii) said control section of said power supply supplying power to said at least one medium pressure mercury lamp in order to thereby selectively control either (i) said pump or (ii) said radiation source in response to the optical transmission measured by said transmission measuring means.

28. The apparatus as defined in claim 27, wherein:

said throughflow photoreactor contains an outlet for discharging irradiated medium;

said throughflow photoreactor includes at least one irradiation chamber; and said optical transmission measuring means being selectively arranged either (i) at said outlet or (ii) at the end of said at least one irradiation chamber as viewed in said throughflow direction.

29. The apparatus as defined in claim 28, wherein:

said throughflow photoreactor is an annular dual chamber throughflow photoreactor including an inner irradiation chamber facing said at least one medium pressure mercury lamp and an outer irradiation chamber disposed remote from said at least one medium pressure mercury lamp;

said inner irradiation chamber and said outer irradiation chamber being in flow communication and being throughpassed by said medium in countercurrent fashion;

said transmission measuring means being arranged close to the end of said outer irradiation chamber as viewed in the direction of said throughflow; and said control means selectively controlling either (i) said power supply of said pump or (ii) said power supply of said at least one medium pressure mercury lamp in a manner such that the optical transmission measured by said transmission measuring means is adjusted to a value in the range of 40% to 63%.

30. The apparatus as defined in claim 19, further including:

circulation means for circulating said medium through said at least one throughflow photoreactor;

said circulation means including a circulating pump having an input side and an output side;

said at least one throughflow photoreactor having inlet means for infeeding said medium and outlet means for outfeeding irradiated medium;

said outlet means being connected to said input side of said circulating pump;

said inlet means being connected to said output side of said circulating pump; and means for adding said radical forming absorber to said circulation means.

31. The apparatus as defined in claim 30, further including cooling means connected in said circulation means.

32. The apparatus as defined in claim 19, wherein:

said at least one throughflow photoreactor constitutes a substantially vertically disposed, substantially cylindrical tank photoreactor having an inlet and an outlet and defining a central longitudinal axis;

said transparent wall made of quartz glass constituting a spacer tube having a closed end and defining an irradiation unit conjointly with said elongate radiation source;

an annular array of a multiple number of said irradiation units disposed at a predetermined radial spacing from said central longitudinal axis of said tank photoreactor;

oxygen supply means connecting an oxygen source and said tank photoreactor; and said oxygen supply means including a multiple number of oxygen infeed means closely spaced from said closed ends of the spacer tubes in respective ones of said multiple number of irradiation units.

33. The apparatus as defined in claim 32, wherein an additional irradiation unit extends along said central longitudinal axis of said tank photoreactor.

34. The apparatus as defined in claim 32, further including:

a mixing chamber receiving said medium and connected to said inlet of said tank photoreactor;

said mixing chamber including a preheater;

a cooler connected to said outlet means of said tank photoreactor for receiving irradiated medium;

said cooler being connected to a coolant circulation; and said coolant circulation including said preheater of said mixing chamber.

35. An irradiation unit generating radiation including UV radiation in the wavelength range below 280 nm for oxidative photopurification of an optically transparent medium, which is contaminated by at least one oxidizable carbon compound and contains a dissolved radical forming absorber which forms two free radicals upon photolysis by said UV radiation in the wavelength range below 280 nm, said irradiation unit comprising:

an elongate radiation source for emitting radiation for oxidative photopurification;

said elongate radiation source comprises at least one medium pressure mercury lamp defining a lengthwise axis and emitting radiation including UV radiation in the wavelength range below 280 nm; and a quartz glass spacer tube which is transparent for said radiation including UV radiation in the wavelength range below 280 nm and coaxially surrounds said at least one medium pressure mercury lamp at a radial spacing of more than 3 cm from said lengthwise axis of said at least one medium pressure mercury lamp.

36. The irradiation unit as defined in claim 35, wherein said radial spacing of said spacer tube from said lengthwise axis of said at least one medium pressure mercury lamp is in the range of more than 3 cm to 13 cm.

37. The irradiation unit as defined in claim 36, wherein said radial spacing of said spacer tube from said lengthwise axis of said at least one medium pressure mercury lamp is in the range of 4 cm to 9 cm.

38. The irradiation unit as defined in claim 35, further including an envelope tube made of quartz glass and coaxially surrounding said at least one medium pressure mercury lamp at a radial distance up to 3 cm from said lengthwise axis of said at least one medium pressure mercury lamp.

39. The irradiation unit as defined in claim 35, wherein said at least one medium pressure mercury lamp having a rated power in the range of 10 W to 250 W per cm arc length for operation at a maximum power input in the range of 65% to 85% of said rated power.

40. The irradiation unit as defined in claim 35, further including:
retaining means for mounting said irradiation unit at a photoreactor for oxidative photopurification; and
connecting means for connecting said elongate radiation source to an electric power supply.

* * * * *